(12) United States Patent
Watanabe et al.

(10) Patent No.: US 6,218,392 B1
(45) Date of Patent: *Apr. 17, 2001

(54) FUSED PYRIDAZINE COMPOUNDS

(75) Inventors: Nobuhisa Watanabe; Yasuhiro Kabasawa; Yasutaka Takase; Fumihiro Ozaki; Keiji Ishibashi; Kazuki Miyazaki; Masayuki Matsukura; Shigeru Souda; Kazutoshi Miyake; Hiroki Ishihara; Kohtaro Kodama; Hideyuki Adachi, all of Ibaraki (JP)

(73) Assignee: Eisai Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/161,946

(22) Filed: Sep. 29, 1998

Related U.S. Application Data

(62) Division of application No. 08/619,621, filed as application No. PCT/JP95/01575 on Aug. 8, 1995, now Pat. No. 5,849,741.

(30) Foreign Application Priority Data

Aug. 9, 1994 (JP) .................................................. 6-187128
Dec. 20, 1994 (JP) .................................................. 6-316337

(51) Int. Cl.[7] .................. A61K 31/502; A61K 31/5377; C07D 237/34; C07D 413/04
(52) U.S. Cl. .................. 514/248; 514/234.5; 544/119; 544/237
(58) Field of Search .................. 544/237, 119; 514/248, 234.5

(56) References Cited

U.S. PATENT DOCUMENTS

| 3,494,921 | 2/1970 | Dorman | 544/236 |
| 3,971,783 | 7/1976 | Barnish et al. | 514/259 |
| 5,089,494 | 2/1992 | Iwase et al. | 544/237 |
| 5,324,727 | 6/1994 | Iwase et al. | 544/237 |
| 5,462,941 | 10/1995 | Iwase et al. | 544/237 |

FOREIGN PATENT DOCUMENTS

| 0449203 | 10/1991 | (EP) . |
| 0579496 | 1/1994 | (EP) . |
| 1418822 | 12/1975 | (GB) . |
| 48-86894 | 1/1973 | (JP) . |
| 50-29582 | 3/1975 | (JP) . |
| 2129180 | 5/1990 | (JP) . |
| 0048664 | 3/1991 | (JP) . |
| 3106874 | 5/1991 | (JP) . |
| 6135938 | 5/1994 | (JP) . |
| 8809790 | 12/1988 | (WO) . |
| 9420508 | 9/1994 | (WO) . |

OTHER PUBLICATIONS

Kormendy et al., Acta Chimica Hungarica 112(4), 487–499 (1983).
Lee et al., Drugs Exptl. Clin. Res. XVII(7) 323–336 (1991).
Abstract for WO 93/07124 (Apr. 15, 1993).

*Primary Examiner*—Emily Bernhardt
(74) *Attorney, Agent, or Firm*—Birch, Stewart, Kolasch & Birch, LLP.

(57) ABSTRACT

A fused pyridazine compound represented by the following general formula (I) or a pharmacologically acceptable salt thereof which exhibits an inhibitory activity against cyclic GMP phosphodiesterase (hereinafter referred to as "cGMP-PDE").

The compounds are useful as preventive and therapeutic agents for diseases for which a cGMP-PDE inhibiting action is efficacious, for example, ischemic heart diseases such as angina pectoris, myocardial infarct and chronic and acute cardiac failure, pulmonary hypertension, arteriosclerosis and bronchial asthma.

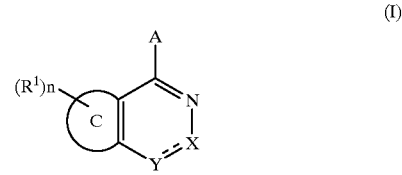

(I)

6 Claims, No Drawings

FUSED PYRIDAZINE COMPOUNDS

This application is a divisional of application Ser. No. 08/619,621, filed on Apr. 9, 1996 now U.S. Pat. No. 5,849, 741. Application Ser. No. 08/619,621 is the national phase of PCT International Application No. PCT/JP95/01575 filed on Aug. 8, 1995 under 35 U.S.C. § 371. The entire contents of each of the above identified applications are hereby incorporated by reference.

FIELD OF THE INVENTION

The present invention relates to a novel fused pyridazine compound. In particular, the present invention relates to a novel fused pyridazine compound which is useful as drug.

DESCRIPTION OF RELATED BACKGROUND ART

Recently, studies on compounds exhibiting inhibitory activity against cyclic GMP phosphodiesterase (hereinafter referred to as "cGMP-PDE") have proceeded and attempts have been made to apply such compounds to the prevention and treatment of circulatory failures such as hypertension, angina pectoris and myocardial infarct.

Known examples of the compound usable in the prevention and treatment of circulatory failures include quinazoline compounds disclosed in JP-A-29582/1975, 4H-3,1-benzoxazin-4-one compounds disclosed in WO 88/09790, 1H-2,3,4,5-tetra-hydroimidazo[2,1-b]quinazolin-2-one and 1,2,3,4,5,6-hexahydropyrimido[2,1-b]quinazolin-2-one disclosed in JP-A-86894/1973, nitrogenous heterocyclic compounds disclosed in WO 93/07124 and 4-aminoquinazoline derivatives disclosed in EP 579496.

However, most of the compounds described above are not on the market and many of them have problems of solubility, in vivo dynamics and toxicity which must be solved prior to the use as drugs.

DISCLOSURE OF THE INVENTION

Under the above circumstances, the inventors of the present invention have started their studies for the purpose of finding a compound which exhibits an excellent cGMP-PDE inhibiting activity, has such a high water solubility as to be well absorbed into the living body, and is less toxic.

As a result of the studies, they have found that the above object can be attained by a fused pyridazine compound represented by the following general formula (I) or a pharmacologically acceptable salt thereof. The present invention has been accomplished on the basis of this finding.

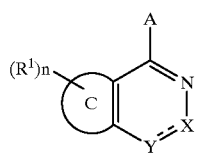
(I)

{wherein ring C represents a five- or six-membered ring which may contain a heteroatom;

n is an integer of 0 to 4;

$R^1$ represents a halogen atom, an optionally substituted lower alkyl group, optionally substituted lower alkoxy group, an optionally substituted cycloalkyl group, a nitro group, a cyano group, —$NR^2R^3$ (wherein $R^2$ and $R^3$ represent each independently a hydrogen atom, an optionally substituted lower alkyl group, an acyl group, optionally substituted arylalkyl group or an optionally substituted heteroarylalkyl group, or alternatively $R^2$ and $R^3$ together with the nitrogen atom to which they are bonded may form a ring which may be substituted), —O—$R^9$ (wherein $R^9$ represents a hydrogen atom, an optionally substituted lower alkyl group, an acyl group, an optionally substituted arylalkyl group or an optionally substituted heteroarylalkyl group), —S—$R^{10}$ (wherein $R^{10}$ represents a hydrogen atom, an optionally substituted lower alkyl group, an acyl group, an optionally substituted arylalkyl group or an optionally substituted heteroarylalkyl group),

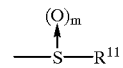

(wherein $R^{11}$ represents a hydrogen atom, a lower alkyl group or an amino group; and m is an integer of 0 to 2), or an optionally protected carboxyl group, with the proviso that when n is 2 to 4, $R^1$'s represent each independently a substituent selected from among those described above;

A represents a hydrogen atom, a halogen atom, —$NR^4R^5$ (wherein $R^4$ and $R^5$ represent each independently a hydrogen atom, an optionally substituted lower alkyl group, an acyl group, an optionally substituted arylalkyl group or an optionally substituted heteroarylalkyl group, or alternatively $R^4$ and $R^5$ together with the nitrogen atom to which they are bonded may form a ring which may be substituted), an optionally substituted aryl group, an optionally substituted heteroaryl group, an optionally substituted arylalkyl group or an optionally substituted heteroarylalkyl group;

X represents —$NR^6$— (wherein $R^6$ represents a hydrogen atom, an optionally substituted lower alkyl group, an optionally substituted arylalkyl group or an optionally substituted heteroarylalkyl group) or —N═;

Y represents —CO— or —CB═ (wherein B represents a hydrogen atom, a halogen atom, —$NR^7R^8$ (wherein $R^7$ and $R^8$ represent each independently a hydrogen atom, an optionally substituted lower alkyl group, an acyl group, an optionally substituted arylalkyl group or an optionally substituted heteroarylalkyl group, or alternatively $R^7$ and $R^8$ together with the nitrogen atom to which they are bonded may form a ring which may be substituted), —O—$R^{12}$ (wherein $R^{12}$ represents a hydrogen atom, an optionally substituted lower alkyl group, an acyl group, an optionally substituted arylalkyl group or an optionally substituted heteroarylalkyl group), —S—$R^{13}$ (wherein $R^{13}$ represents a hydrogen atom, an optionally substituted lower alkyl group, an acyl group, an optionally substituted arylalkyl group or an optionally substituted heteroarylalkyl group), an optionally substituted aryl group, an optionally substituted heteroaryl group, an optionally substituted arylalkyl group or an optionally substituted heteroarylalkyl group]; and the symbol -------- represents a double bond or a single bond, with the proviso that the cases wherein C represents a benzene ring and n is 0) are excepted.}

In the above definition of the general formula (I), the lower alkyl group constituting the optionally substituted lower alkyl as defined with respect to $R^1$, $R^2$, $R^3$, $R^4$, $R^5$, $R^6$, $R^7$, $R^8$, $R^9$, $R^{10}$, $R^{11}$, $R^{12}$ and $R^{13}$ may be a linear or branched lower alkyl group having 1 to 6 carbon atoms, and examples thereof include methyl, ethyl, n-propyl, isopropyl, n-butyl, isobutyl, 1-methylpropyl, tert-butyl, n-pentyl, 1-ethylpropyl, isoamyl and n-hexyl. The substituent constituting it includes a hydroxyl group, a nitro group, an amino group, a cyano group, acyl groups such as an acetyl group and a benzoyl group; lower alkoxy groups such as a methoxy group and an ethoxy group; halogen atoms such as a fluorine atom, a chlorine atom, a bromine atom and an iodine atom; and an optionally protected carboxyl group. One or more of these substituents may be bonded to one or more carbon atoms of the lower alkyl group.

The lower alkoxy group constituting the optionally substituted lower alkoxy group as defined with respect to $R^1$ may be one derived from the above lower alkyl group, and examples thereof include a methoxy group, an ethoxy group and a propoxy group.

The substituent constituting it includes a hydroxyl group, a nitro group, an amino group, a cyano group, acyl groups such as an acetyl group and a benzoyl group; lower alkoxy groups such as a methoxy group and an ethoxy group; halogen atoms such as a fluorine atom, a chlorine atom, a bromine atom and an iodine atom; and an optionally protected carboxyl group. One or more of these substituents may be bonded to one or more carbon atoms of the lower alkoxy group.

The cycloalkyl group constituting the optionally substituted cycloalkyl group as defined with respect to $R^1$ may be one having 3 to 8 carbon atoms, while the substituent constituting it includes a hydroxyl group, a nitro group, an amino group, a cyano group, an acyl groups such as an acetyl group and a benzoyl group; lower alkoxy groups such as a methoxy group and an ethoxy group; halogen atoms such as a fluorine atom, a chlorine atom, a bromine atom and an iodine atom; and an optionally protected carboxyl group. One or more of these substituents may be bonded to one or more carbon atoms of the cycloalkyl group.

The acyl group as defined with respect to $R^2$, $R^3$, $R^4$, $R^5$, $R^7$, $R^8$, $R^9$, $R^{10}$, $R^{12}$ and $R^{13}$ may be one derived from an aliphatic, aromatic or acyl group derived from heterocyclic ring, and examples thereof include lower alkanoyl groups such as a formyl group, an acetyl group, a propionyl group, a butyryl group, a valeryl group, an isovaleryl group and a pivaloyl group; aroyl groups such as a benzoyl group, a toluoyl group and a naphthoyl group; and heteroaroyl groups such as a furoyl group, a nicotinoyl group and an isonicotinoyl group. In short, the group may be one derived from any carboxylic acid. Among these, a formyl group, an acetyl group and a benzoyl group are preferable.

The aryl group constituting the optionally substituted aryl as defined with respect to A and B may be one derived from an aromatic ring, and examples thereof include phenyl, 1-naphthyl, 2-naphthyl and anthracenyl. The substituent constituting it includes a hydroxyl group, a nitro group, an amino group, a cyano group, acyl groups such as an acetyl group and a benzoyl group; a lower alkoxy group such as a methoxy group and an ethoxy group; halogen atoms such as a fluorine atom, a chlorine atom, a bromine atom and an iodine atom; and an optionally protected carboxyl group.

The heteroaryl group constituting the optionally substituted heteroarylalkyl group as defined with respect to A and B may be a mono- or poly-cyclic group having one or more heteroatoms selected from among nitrogen, sulfur and oxygen atom. Examples thereof include pyridyl, pyrrolyl, imidazolyl, pyrazolyl, pyrazyl, pyrimidyl, pyridazyl, thienyl, pyranyl, isothiazolyl, isoxazolyl, furazanyl, benzothienyl, furyl, indolyl, indolizinyl, isoindolyl, benzothiazolyl, benzoimidazolyl and quinazolyl. The substituent constituting it includes a hydroxyl group, a nitro group, an amino group, a cyano group, acyl groups such as an acetyl group and a benzoyl group; lower alkoxy groups such as a methoxy group and an ethoxy group; halogen atoms such as a fluorine group, a chlorine group, a bromine group and an iodine group; and an optionally protected carboxyl group.

As defined above, $R^7$ and $R^8$ together with the nitrogen atom to which they are bonded may form a ring which may be substituted, and examples of the ring include piperidinyl, pyrrolidinyl and piperazinyl. The substituent for the ring includes a hydroxyl group, an optionally substituted amino group, an aminoalkyl group, a nitro group, a nitroalkyl group, a lower alkoxy group, a lower alkoxyalkyl group, a hydroxyalkyl group, an optionally protected carboxyl group and an optionally protected carboxyalkyl group, among which a hydroxyl group, a hydroxymethyl group, a hydroxyethyl group, a carboxymethyl group and a carboxyethyl group are preferable.

The aryl group constituting the optionally substituted arylalkyl group as defined with respect to $R^2$, $R^3$, $R^4$, $R^5$, $R^6$, $R^7$, $R^8$, $R^9$, $R^{10}$, $R^{12}$, $R^{13}$ and Y may be one derived from an aromatic ring, and examples thereof include phenyl, 1-naphthyl, 2-naphthyl and anthracenyl. The group corresponding to the "alkyl" moiety constituting it may be one derived from the above lower alkyl group. The substituent constituting it includes a hydroxyl group, a nitro group, an amino group, a cyano group, acyl groups such as an acetyl group and a benzoyl group; lower alkoxy groups such as a methoxy group and an ethoxy group; halogen atoms such as a fluorine atom, a chlorine group, a bromine atom and an iodine group; and an optionally protected carboxyl group.

The heteroaryl group constituting the optionally substituted heteroarylalkyl as defined with respect to $R^2$, $R^3$, $R^4$, $R^5$, $R^6$, $R^7$, $R^8$, $R^9$, $R^{10}$, $R^{12}$, $R^{13}$ and Y may be a mono- or poly-cyclic group having one or more heteroatoms selected from among a nitrogen atom, a sulfur atom and an oxygen atom, and examples thereof include pyridyl, pyrrolyl, imidazolyl, pyrazolyl, pyrazyl, pyrimidyl, pyridazyl, thienyl, pyranyl, isothiazolyl, isoxazolyl, furazanyl, benzothienyl, furyl, indolyl, indolizinyl, isoindolyl, benzothiazolyl, benzoimidazolyl and quinazolyl. The group corresponding to the "alkyl" moiety constituting it may be one derived from the above lower alkyl group. The substituent constituting it includes a hydroxyl group, a nitro group, an amino group, a cyano group, acyl groups such as an acetyl group and a benzoyl group; lower alkoxy groups such as a methoxy group and an ethoxy group; halogen atoms such as a fluorine atom, a chlorine atom, a bromine atom and an iodine group; and an optionally protected carboxyl group.

The halogen atom as defined with respect to $R^1$, $R^{12}$, $R^{13}$ and $R^{14}$ includes a fluorine atom, a chlorine atom, a bromine atom and an iodine atom.

The pharmacologically acceptable salt according to the present invention includes inorganic acid salts such as hydrochloride, sulfate, hydrobromide and phosphate; and organic acid salts such as formate, acetate, trifluoroacetate, maleate, fumarate, tartrate, methanesulfonate, benzenesulfonate and toluenesulfonate.

Although several compounds according to the present invention form hydrates, it is needless to say that the hydrates fall within the scope of the present invention.

Among the compounds of the present invention, fused pyridazine compounds represented by the following general formula (II) and pharmacologically acceptable salts thereof are preferable:

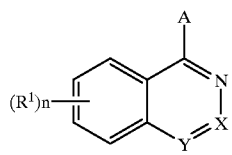

(II)

{wherein R¹ represents a hydrogen atom, a halogen atom, an optionally substituted lower alkyl group, an optionally substituted lower alkoxy group, an optionally substituted cycloalkyl group, a nitro group, a cyano group, —NR²R³ (wherein R² and R³ represent each independently a hydrogen atom, an optionally substituted lower alkyl group, an acyl group, an optionally substituted arylalkyl group or an optionally substituted heteroarylalkyl group, or alternatively R² and R³ together with the nitrogen atom to which they are bonded may form a ring which may be substituted), —O—R⁹ (wherein R⁹ represents a hydrogen group, an optionally substituted lower alkyl group, an acyl group, an optionally substituted arylalkyl group or an optionally substituted heteroarylalkyl group), —S—R¹⁰ (wherein R¹⁰ represents a hydrogen atom, an optionally substituted lower alkyl group, an acyl group, an optionally substituted arylalkyl group or an optionally substituted heteroarylalkyl group),

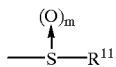

(wherein R¹¹ represents a hydrogen atom, a lower alkyl group or an amino group: and m is an integer of 0 to 2), or optionally protected carboxyl, with the proviso that when n is 2 to 4, R¹'s represent each independently a substituent selected from among those described above;

A represents a hydrogen atom, a halogen atom, —NR⁴R⁵ (wherein R⁴ and R⁵ represent each independently a hydrogen atom, an optionally substituted lower alkyl atom, an acyl group, an optionally substituted arylalkyl group or an optionally substituted heteroarylalkyl group, or alternatively R⁴ and R⁵ together with the nitrogen atom to which they are bonded may form a ring which may be substituted), an optionally substituted aryl group, an optionally substituted heteroaryl group, an optionally substituted arylalkyl group or an optionally substituted heteroarylalkyl group;

X represents —NR⁶— (wherein R⁶ represents a hydrogen atom, an optionally substituted lower alkyl group, an optionally substituted arylalkyl group or an optionally substituted heteroaryl group) or —N═;

Y represents —CO— or —CB═ [wherein B represents a hydrogen group, a halogen atom, —NR⁷R⁸ (wherein R⁷ and R⁸ represent each independently a hydrogen atom, an optionally substituted lower alkyl group, an acyl group, an optionally substituted arylalkyl group or an optionally substituted heteroarylalkyl group, or alternatively R⁷ and R⁸ together with the nitrogen atom to which they are bonded may form a ring which may be substituted), —O—R¹² (wherein R¹² represents a hydrogen atom, an optionally substituted lower alkyl group, an acyl group, an optionally substituted arylalkyl group or an optionally substituted heteroarylalkyl group), —S—R¹³ (wherein R¹³ represents a hydrogen atom, an optionally substituted lower alkyl group, an acyl group, an optionally substituted arylalkyl group or an optionally substituted heteroarylalkyl group), an optionally substituted aryl group, an optionally substituted heteroaryl group, an optionally substituted arylalkyl group or an optionally substituted heteroarylalkyl group]; and the symbol ——————
represents a double bond or a single bond, with the proviso that the cases wherein ring C represents a benzene ring and n is 0 are excepted.

Among the above preferable compounds, fused pyridazine compounds represented by the following general formula (III) and pharmacologically acceptable salts thereof are desirable:

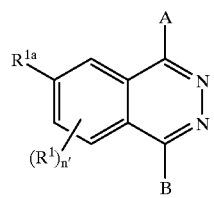

(III)

[wherein R¹ᵃ represents a halogen atom, an optionally substituted lower alkyl group, an optionally substituted lower alkoxy group, an optionally substituted cycloalkyl group, a nitro group, a cyano group or —NR²R³ (wherein R² and R³ represent each independently a hydrogen atom, an optionally substituted lower alkyl group, an acyl group, an optionally substituted arylalkyl group or an optionally substituted heteroarylalkyl group, or alternatively R² and R³ together with the nitrogen atom to which they are bonded may form a ring which may be substituted);

R¹ represents a hydrogen atom, a halogen atom, an optionally substituted lower alkyl group, an optionally substituted lower alkoxy group, an optionally substituted cycloalkyl group, a nitro group, a cyano group, —NR²R³ (wherein R² and R³ represent each independently a hydrogen ayom, an optionally substituted lower alkyl group, an acyl group, an optionally substituted arylalkyl group or an optionally substituted heteroarylalkyl group, or alternatively R² and R³ together with the nitrogen atom to which they are bonded may form a ring which may be substituted), —O—R⁹ (wherein R⁹ represents a hydrogen atom, an optionally substituted lower alkyl group, an acyl group, an optionally substituted arylalkyl group or an optionally substituted heteroarylalkyl group), —S—R¹⁰ (wherein R¹⁰ represents a hydrogen atom, an optionally substituted lower alkyl group, an acyl group, an optionally substituted arylalkyl group or an optionally substituted heteroarylalkyl group),

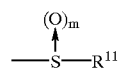

(wherein R¹¹ represents a hydrogen atom, a lower alkyl group or an amino group; and m is an integer of 0 to 2), or an optionally protected carboxyl group, with the proviso that when n is 2 to 4, R¹'s represent each independently a substituent selected from among those described above;

A represents a hydrogen atom, a halogen atom, —NR⁴R⁵ (wherein R⁴ and R⁵ represent each independently a hydrogen atom, an optionally substituted lower alkyl group, an acyl group, an optionally substituted arylalkyl group or an optionally substituted heteroarylalkyl group, or alternatively R⁴ and R⁵ together with the nitrogen atom to which they are bonded may form a ring which may be substituted), an optionally substituted aryl group, an optionally substituted heteroaryl group, an optionally substituted arylalkyl group or an optionally substituted heteroarylalkyl group; and B represents a hydrogen atom, a halogen atom, —NR$^7$R$^8$ (wherein R$^7$ and R$^8$ represent each independently a hydrogen atom, an optionally substituted lower alkyl group, an acyl group, an optionally substituted arylalkyl group or an optionally substituted heteroarylalkyl group, or alternatively R$^7$ and R$^8$ together with the nitrogen atom to which they are bonded may form a ring which may be substituted), —O—R$^{12}$ (wherein R$^{12}$ represents a hydrogen atom, an optionally substituted lower alkyl group, an acyl group, an optionally substituted arylalkyl group or an optionally substituted heteroarylalkyl group), —S—R$^{13}$ (wherein R$^{13}$ represents a hydrogen, an optionally substituted lower alkyl group, an acyl group, an optionally substituted arylalkyl group or an optionally substituted heteroarylalkyl group), an optionally substituted aryl group, an optionally substituted heteroaryl group, an optionally substituted arylalkyl group or an optionally substituted heteroarylalkyl group].

Further, fused pyridazine compounds represented by the following general formula (V) and pharmacologically acceptable salts thereof are more desirable:

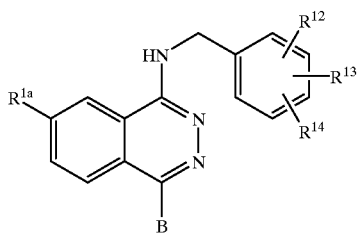

(V)

(wherein R$^{1a}$ represents a halogen atom, an optionally substituted lower alkyl group, an optionally substituted lower alkoxy group, an optionally substituted cycloalkyl group, a nitro group, a cyano group or —NR$^2$R$^3$ (wherein R$^2$ and R$^3$ represent each independently a hydrogen atom, an optionally substituted lower alkyl group, an acyl group, an optionally substituted arylalkyl group or an optionally substituted heteroarylalkyl group, or alternatively R$^2$ and R$^3$ together with the nitrogen atom to which they are bonded may form a ring which may be substituted);

B represents a hydrogen atom, a halogen atom, —NR$^7$R$^8$ (wherein R$^7$ and R$^8$ represent each independently a hydrogen atom, an optionally substituted lower alkyl group, an acyl group, an optionally substituted arylalkyl group or an optionally substituted heteroarylalkyl group, or alternatively R$^7$ and R$^8$ together with the nitrogen atom to which they are bonded may form a ring which may be substituted), —O—R$^{12}$ (wherein R$^{12}$ represents a hydrogen atom, an optionally substituted lower alkyl group, an acyl group, an optionally substituted arylalkyl group or an optionally substituted heteroarylalkyl group), —S—R$^{13}$ (wherein R$^{13}$ represents a hydrogen atom, an optionally substituted lower alkyl group, an acyl group, an optionally substituted arylalkyl group or an optionally substituted heteroarylalkyl group), an optionally substituted aryl group, an optionally substituted heteroaryl group, an optionally substituted arylalkyl group or an optionally substituted heteroarylalkyl group; and R$^{12}$, R$^{13}$ and R$^{14}$ represent each independently a hydrogen atom, a halogen atom, an optionally substituted lower alkyl group or an optionally substituted lower alkoxy group, or alternatively two of R$^{12}$, R$^{13}$ and R$^{14}$ which are bonded to the carbon atoms adjacent to each other may be united to form methylenedioxy or ethylenedioxy).

Furthermore, compounds represented by the following general formula (V') are most desirable:

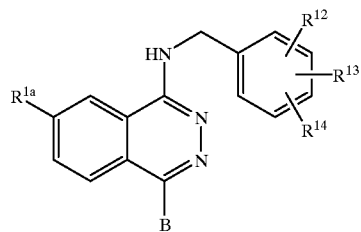

(V')

(wherein R$^{1a}$ represents a halogen atom, a nitro group or a cyano group, preferably a cyano group; B desirably represents —NR$^7$R$^8$ (wherein R$^7$ and R$^8$ represent each independently a hydrogen atom, an optionally substituted lower alkyl group, an acyl group, an optionally substituted arylalkyl group or an optionally substituted heteroarylalkyl group, or alternatively R$^7$ and R$^8$ together with the nitrogen atom to which they are bonded may form a ring which may be substituted), more desirably —NR$^7$R$^8$ (wherein R$^7$ and R$^8$ together with the nitrogen atom to which they are bonded form a ring which is preferably substituted with a hydroxyl group, a carboxyl group, a hydroxyalkyl group, a carboxyalkyl group or the like, still preferably at the position 4. It is most desirable that the substituent is a hydroxyl group or hydroxyalkyl group.

The compounds of the present invention can be readily prepared by known processes or combinations of known processes. Several main processes for the preparation of the compounds of the present invention will now be described, though it is needless to say that the compounds of the present invention are not limited to those prepared by these processes.

Preparation process 1

A compound represented by the general formula (I) wherein A and B are each a halogen atom can be prepared by the following process:

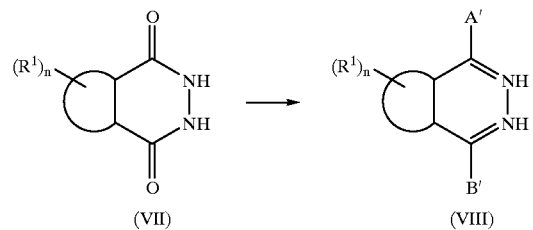

(wherein A' and B' represent each independently a halogen atom; and R$^1$ and n are each as defined above)

Specifically, the above compound can be prepared by halogenating a corresponding 1,4-phthalazinedione derivative. This halogenation can be conducted in a conventional manner. Examples of the chlorinating agent usable in this case include phosphorus pentachloride, phosphorus oxychloride and mixture of both. Although the halogenation can be conducted without any solvent, any solvent inert to the halogenation may be used. In some cases, the use of a tertiary amine such as diisopropylethylamine or N,N-dimethylformamide gives better results. The reaction temperature preferably ranges from about room temperature to about 150° C.

Preparation process 2

A compound represented by the general formula (I) wherein ring C represents a benzene ring; A and B represent each independently a halogen atom; $R^1$ represents a cyano group; and n is 1 can be prepared also by the following process:

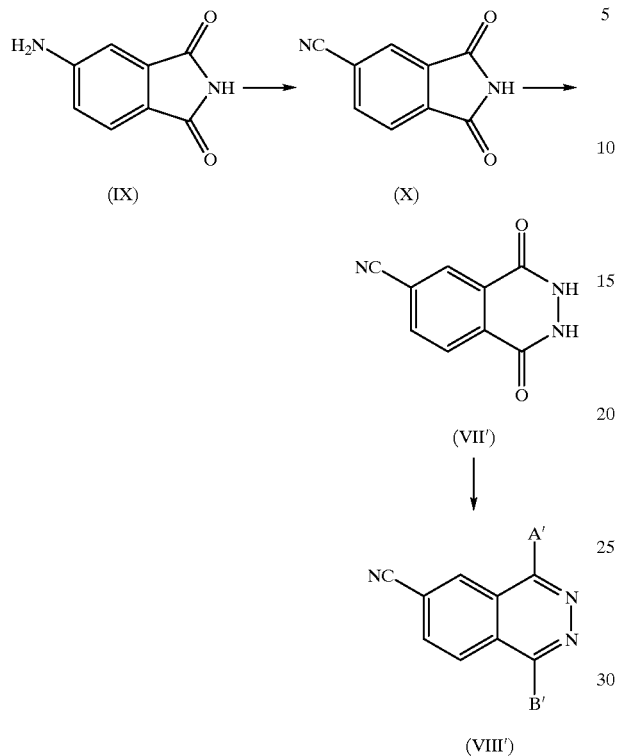

(wherein A' and B' are each as defined above)

(1st step)

In this step, the amino group of 4-amino-phthalimide is converted into a cyano group. This conversion is preferably conducted by the Sandmeyer reaction, though it may be conducted by any conventional process. According to the Sandmeyer reaction, the conversion is conducted by converting 4-aminophthalimide into a diazonium salt in a conventional manner and thereafter reacting the diazonium salt with a nucleophilic reagent such as copper salt to replace the diazonium group by a cyano group. Although commercially available copper cyanide may be used in this reaction, better results can be attained by the use of the copper cyanide prepared from potassium cyanide and cuprous chloride just before use.

(2nd step)

In this step, the phthalimide derivative prepared in the 1st step is converted into a corresponding 1,4-phthalazinidione. This conversion can be conducted according to the process described in Castle: "HETEROCYCLIC COMPOUNDS", Vol.27.

(3rd step)

In this step, the 1,4-phthalazinedione prepared in the above 2nd step is prepared according to Preparation process 1.

Preparation process 3

A compound represented by the general formula (I) wherein ring C represents a benzene ring; A and B represent each independently a halogen atom; $R^1$ represents a cyano group; and n is 1 can be prepared also by the following process:

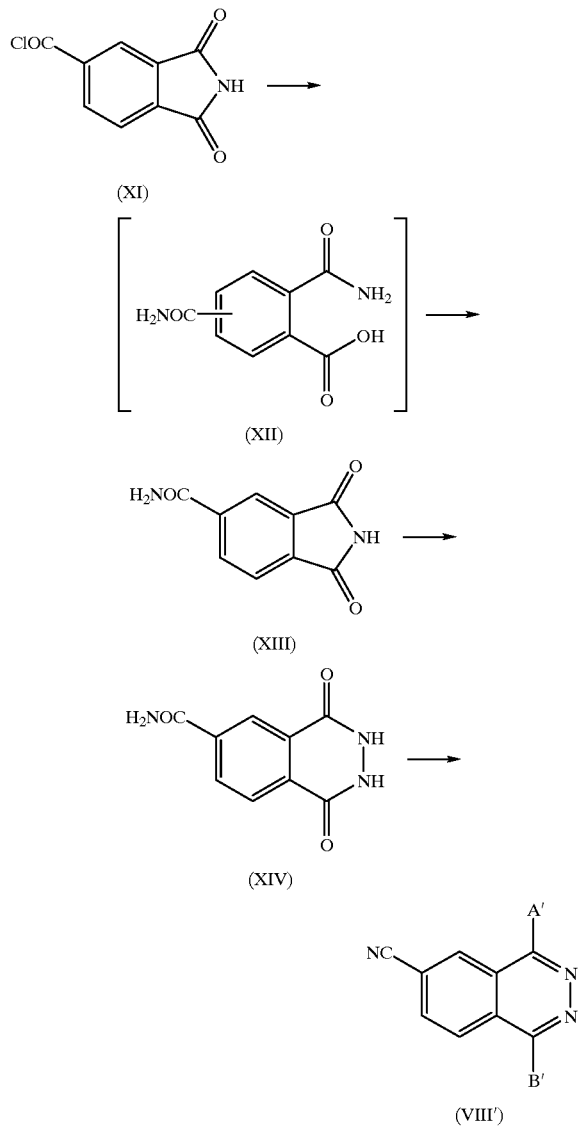

(wherein A' and B' are each as defined above)

(1st step)

In this step, 4-carbamoylphthalimide is prepared by reacting trimellitoyl chloride with ammonia and dehydrating the obtained product. Specifically, this reaction is conducted by reacting trimellitoyl chloride with aqueous ammonia either without any solvent or in a state dissolved in a solvent at a temperature ranging from about −15° C. to room temperature. The solvent to be used in this case is preferably acetone, dichloromethane, chloroform or ethyl acetate, though any organic solvent inert to the reaction may be used. The resulting reaction mixture is treated with an acid to give a mixture comprising 2,4-dicarbamoylbenzoic acid and 2,5-dicarbamoylbenzoic acid. This mixture is further treated in the absence or presence of a solvent for 0.5 to 24 hours to give the objective compound. This treatment is conducted at room temperature to about 200° C. The solvent to be used in this treatment is preferably N-methyl-2-pyrrolidinone, though any solvent inert to the reaction may be used.

(2nd step)

In this step, the phthalimide derivative prepared in the above 1st step is converted into a phthalazinedione in a conventional manner.

This conversion can be conducted by a conventional process such as reaction with hydrazine hydrate or the like. The reaction temperature is preferably 0° C. to room temperature.

(3rd step)

In this step, the 6-carbamoyl-2,3-dihydro-1,4-phthalazinedione prepared in the 2nd step is converted into 6-cyano-1,4-dichlorophthalazine through dehydration and chlorination. The reagent useable in this case includes phosphorus oxychloride, thionyl chloride, phosphorus pentachloride and mixtures of two or more of them. The reaction temperature may range from room temperature to the boiling point of the reagent and the reaction time is about 0.5 to 36 hours. In some cases, better results can be attained by the addition of N,N-dimethylformamide or a tertiary amine such as diisopropylethylamine.

Preparation process 4

A compound represented by the formula (I) wherein A represents —$NR^2R^3$ (wherein $R^2$ and $R^3$ represent each independently a hydrogen atom, an optionally substituted lower alkyl group, an acyl group, an optionally substituted arylalkyl group or an optionally substituted heteroarylalkyl group, or alternatively $R^2$ and $R^3$ together with the nitrogen atom to which they are bonded may form a ring which may be substituted) and B represents a halogen atom can be prepared by the following process:

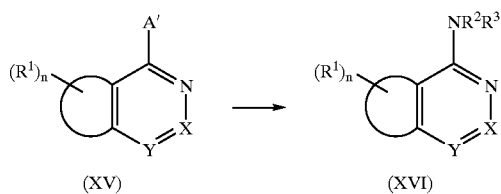

(wherein A' represents a halogen atom; and $R^1$, $R^2$, $R^3$, X and Y are each as defined above).

Specifically, the above compound is prepared through the conventional substitution reaction. The solvent to be used in the reaction may be any organic one inert to the reaction, and preferable examples of the solvent include alcohols such as isopropyl alcohol; ethers such as tetrahydrofuran and 1,4-dioxane; dimethylformamide, dimethylacetamide and N-methyl-2-pyrrolidinone.

The reaction temperature may preferably range from about room temperature to the refluxing temperature of the solvent.

Better results can be attained by the addition of a salt such as potassium carbonate, sodium carbonate or barium carbonate, or a tertiary amine such as diisopropylethylamine or DBU. In particular, the addition of a tertiary amine such as diispropylethylamine or DBU can give the best results.

After the completion of the reaction, the reaction mixture is post-treated in a conventional manner and is freed from undesirable isomers by recrystallization or treatment with a column to give an objective compound.

Preparation process 5

A compound represented by the general formula (I) can be prepared also by the following process:

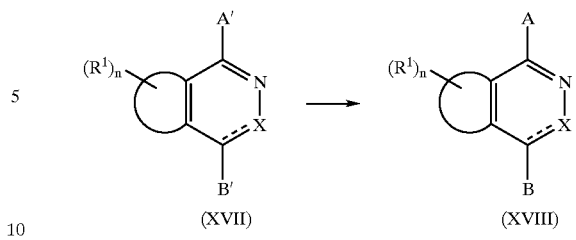

(wherein $R^1$, A, B, A', B', X and n are each as defined above)

According to this process, the objective compound is prepared from the halophthalazine derivative prepared by Preparation process 4 or the like through conventional replacement. The solvent to be used in this case is preferably N-methyl-2-pyrrolidinone, though any solvent inert to the reaction may be used. The reactant B-H is used in excess based on the starting halophthalazine derivative. In some cases, better results can be attained by the addition of an organic base such as diisopropylethylamine, a salt such as potassium carbonate, sodium carbonate or sodium hydrogencarbonate, or an acid such as p-toluenesulfonic acid. Further, still better results can be attained by using hydrochloride of the compound B-H without the above additive.

The reaction temperature may be from about room temperature to the boiling point of the solvent, preferably 100° C. or above.

Preparation process 6

A compound represented by the general formula (I) wherein Y is —CO— can be prepared by the following process:

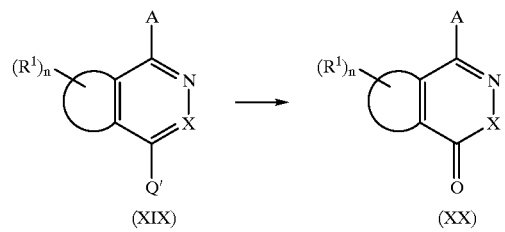

(wherein $R^1$, A, B', X and n are each as defined above).

According to this process, the objective compound is prepared by hydrolyzing a corresponding halophthalazine derivative in a conventional manner. Specifically, the compound can be prepared by heating the corresponding halophthalazine derivative in an acidic or alkaline solution. In some case, better results can be attained when the halophthalazine derivative is stirred under heating at 100 to 200° C. in an organic solvent such as N-methyl-2-pyrrolidinone in the presence of acetic acid for about 0.5 to 12 hours.

Pharmacological Experimental Examples will now be described to illustrate the effects of the present invention.

Pharmacological Experimental Example

Experimental Example 1

Inhibitory Activity Against cGMP-PDE Prepared From Swine Lung

1. Experimental method

The enzyme activity of the cGMP-PDE prepared from swine lung was determined according to the method of Thompson et al. This determination was conducted in the presence of 1 mM EGTA by the use of 1 mM cGMP as substrate. Each compound according to the present invention was dissolved in DMSO and thereafter added to the reaction system to determine the inhibitory activity of the compound. The final concentration of DMSO in the reaction solution was controlled to 5% or below.

The preparation of cGMP-PDE was conducted as follows.

Swine lung was minched, followed by the addition of five times (by volume) as much buffer A (comprising Tris/HCl (20 mM), Mg acetate (2 mM), 2-mercaptoethanol (10 mM), EGTA (0.1 mM) and PMSF (0.2 mM) and adjusted to pH7.4). The resulting mixture was homogenized and centrifuged at 1000×g for 5 minutes. Ammonium sulfate was added to the obtained supernatant and the resulting mixture was centrifuged at 20000×g for 45 minutes to collect a fraction precipitating between 30 and 40% saturation with ammonium sulfate. This fraction was dialyzed against buffer A and passed through a column of DEAE-Toyopearl 650S (a product of Tosoh, Tokyo, Japan). The column was washed with buffer A and subjected to gradient elution with 0.05 to 0.2 M NaCl/buffer A to collect a cGMP-PDE fraction.

This cGMP-PDE fraction was passed through Blue-Sepharose CL-6B (a product of Pharmacia, Uppsala, Sweden). The resulting column was washed with buffer A containing cAMP (10 mM) and NaCl (0.5 M) and eluted with buffer A containing cGMP (10 mM) and NaCl (0.5 M). The obtained fraction was dialyzed, concentrated and stored.

2. Experimental results

The cGMP-PDE inhibitory activities of the compounds of the present invention as determined by the above method are given in Table 1.

| Ex. No. | cGMP-PDE inhibitory activity IC50(nM) | PAP lowering activity |
|---|---|---|
| 1 | 1.7 | ≧3 |
| 4 | 0.18 | — |
| 6 | 0.015 | 10 |
| 7 | 1.2 | 1 |
| 8 | 0.03 | 10 |
| 9 | 0.70 | 10 |
| 10 | 0.01 | 10 |
| 11 | 0.11 | — |
| 17 | ≦0.01 | — |
| 19 | 0.53 | 3–10 |
| 20 | 0.12 | 0.3–1 |
| 25 | 1.41 | 3 |
| 26 | 4.0 | 1 |
| 31 | 3.74 | 1 |
| 32 | 4.4 | 1 |
| 36 | 1.9 | ≧1 |
| 37 | 1.8 | ≦0.33 |
| 43 | 0.37 | 1 |
| 44 | 2.1 | ≦0.33 |
| 49 | 1.88 | 1 |
| 51 | 0.052 | — |
| 52 | 0.10 | 10 |
| 56 | 12.6 | ≧1 |
| 53 | 0.23 | 10 |
| 55 | 4.59 | ≧1 |
| 60 | 20.4 | 1 |
| 67 | 0.32 | 0.33 |

Experimental Example 2

Pulmonary Arterial Pressure Lowering Activity on Anesthetized Thoracotomized Dog by Intravenous Administration 1. Experimental method Male and female hybrid dogs having a weight of about 10 kg were operated under enflurane anesthesia with $N_2O/O_2$ as carrier. Each dog was thoracotomized in the left fourth intercostal space and a pressure transducer (MPC-500 mfd. by Miller) was inserted into the pulmonary artery to determine the pulmonary arterial pressure (PAP). This experiment was conducted with the mean PAP (mPAP) increased by about 10 mmHg by lowering the pressure of oxygen fed by about 40% of the normal one. Each compound according to the present invention was dissolved in Polyethylene glycol 400 (a product of Wako Pure Chemical Industries, Ltd.) in a concentration of 1 mg/ml and, if necessary, further diluted with Polyethylene glycol 400. The resulting solution was intravenously administered to the dog through a polyethylene catheter indwelling in the femoral vein.

2. Experimental results

The PAP lowering activities of the compounds of the present invention as determined by the above method are given in Table 1 in terms of relative ratios to the activity of sodium 1-[chloro-4-(3,4-methylenedioxybenzyl) aminoquinazolin-2-yl]piperidine-4-carboxylate.

Experimental Example 3

In Vitro Platelet Aggregation Inhibiting Activity

1. Experimental method

Blood specimens (10 ml) were collected from the forearm veins of normal male volunteers (age: 30 to 40 years, weight: 60 to 75 kg) who had not taken any drug for at least one week therebefore. In order to prevent blood coagulation, a 3.8% sodium citrate solution (Citral, a product of Yamanouchi Pharmaceutical Co., Ltd.) was added to the blood in an amount of one tenth of the blood volume. The resulting blood was centrifuged at room temperature (22–25° C.) at 700 rpm for 10 minutes to recover a supernatant as platelet rich plasma (PRP). A blood anticoagulant solution (a product of Terumo Corporation) was added to the PRP in a final concentration of 15 v/v%. The resulting mixture was centrifuged at room temperature at 3000 rpm for 10 minutes to give a platelet pellet. This platelet pellet was suspended in physiological saline solution containing 0.1% of EDTA and the resulting suspension was centrifuged again to give another platelet pellet. This pellet was suspended in $Ca^{2+}$-free Tyrode's solution in a final concentration of about $40 \times 10^7$/ml.

The platelet aggregation was determined according to the turbidimetric method of Born et al. with an aggregometer (PAM-8C mfd. by Mebanix). Each compound according to the present invention was dissolved in DMSO in a concentration of 50 mM, followed by serial dilution with $Ca^{2+}$-free Tyrode's solution. The $Ca^{2+}$-free Tyrode's solution was used also as control.

A mixture comprising 25 ml of each of the dilutions of the compound of the present invention prepared above and 200 ml of the washed platelet prepared above was incubated, followed by the addition of 25 ml of a platelet coagulant. The resulting mixture was observed for aggregation. The platelet coagulant used was 3 mg/ml collagen (a product of Hormon-Chemie), 0.3 mM U46619 (a product of Cayman Chemical) or 0.04 U/ml thrombin (a product of Sigma).

The inhibitory activities of the compounds of the present invention were represented in terms of inhibitory ratios based on the aggregation intensity of control (the area of turbidity chart of the aggregometer).

2. Experimental results

The platelet aggregation inhibiting activities of the compounds of the present invention as determined by the above method are given in Table 2 in terms of inhibitory concentrations (mM).

| Ex. No. | Coagulant | | |
|---|---|---|---|
| | collagen | U46619 | thrombin |
| 4 | 11 | | 5.6 |
| 18 (dihydrochloride-free) | 20 | 21 | |
| 32 | 28 | | |
| 43 (hydrochloride) | 61 | 63 | 80 |
| 56 | 55 | 37 | 61 |

It can be understood from the results of the above pharmacological experiments that the compounds of the present invention exhibit cGMP-PDE inhibitory activity, platelet aggregation inhibiting activity and pulmonary arterial pressure lowering activity. Accordingly, the compounds of the present invention are useful as preventive and therapeutic agents for diseases for which cGMP-PDE inhibiting action, platelet aggregation inhibiting action or pulmonary arterial pressure lowering action is efficacious. Specific examples of such diseases include ischemic heart diseases such as angina pectoris, myocardial infarct and chronic and acute heart failures; pulmonary hypertension accompanied by pulmonary heart and that not accompanied thereby; thrombosis caused by trauma of vascular wall, arterial sclerosis, vasculitis and so forth; hypertension caused by arterial sclerosis and others; brain circulatory disturbances such as peripheral circulation failure and cerebral infarction; cerebral malfunction; and allergic diseases such as bronchial asthma, atopic dermatitis and allergic rhinitis.

The compounds of the present invention have higher water solubilities than those of the compounds of the prior art having similar activities and structures. Therefore, they are excellent in the migration into the living body in oral administration, which is an advantage of the compounds of the present invention.

Further, the compounds of the present invention are less toxic and highly safe, thus being extremely useful as drugs.

The compound of the present invention may be orally or parenterally administered as a therapeutic or preventive agent for the above diseases. Although the dose thereof is not particularly limited but varies depending upon the symptom, age, sex and drug sensitivity of patient; the method, timing and interval of administration; the properties and kind of preparation; the kind of active ingredient and so forth, the dose per adult a day is preferably about 0.1 to 1000 mg, which may be administered in one to several portions.

The compounds of the present invention can be converted into pharmaceutical preparations by the use of conventional carriers according to conventional processes.

More precisely, a solid preparation for oral administration according to the present invention is prepared by adding a filler and, if necessary, a binder,disintegrator, lubricant, color, corrigent and/or antioxidant to an active ingredient and shaping the obtained mixture into a tablet, coated tablet, granule, power or capsule.

Examples of the filler include lactose, corn starch, sucrose, glucose, sorbitol, crystalline cellulose and silicon dioxide.

Examples of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; and examples of the lubricant include magnesium stearate, talc, polyethylene glycol, silica and hardened vegetable oils.

Examples of the color include those authorized as pharmaceutical additives. Those of the corrigent include cocoa powder, menthol, aromatic powder, mentha oil, borneol and powdered cinnamon bark; and those of the antioxidant include those authorized as pharmaceutical additives such as ascorbic acid and α-tocopherol. Of course, the tablet and granule may be suitably coated with sugar, gelatin or the like, if necessary.

On the other hand, an injection according to the present invention is prepared by adding a pH modifier, buffer, suspending agent, solubilizing agent, stabilizer, tonicity agent, antioxidant and/or preservative to an active ingredient and formulating the mixture into an injection for intravenous, subcutaneous or intramuscular administration by a conventional process. If necessary, the injection may be freeze-dried.

Examples of the suspending agent include methylcellulose, Polysorbate 80, hydroxyethylcellulose, acacia, tragacanth powder, carboxymethylcellulose sodium and polyoxyethylene sorbitan monolaurate.

Further, examples of the solubilizing agent include polyoxyethylene hardened castor oil, Polysorbate 80, nicotinamide and polyoxyethylene sorbitan monolaurate.

Furthermore, examples of the stabilizer include sodium sulfite, sodium metasulfite and ether; and those of the preservative include methyl p-hydroxybenzoate, ethyl p-hydroxybenzoate, sorbic acid, phenol, cresol and chlorocresol.

EXAMPLE

Examples will now be described to facilitate the understanding of the present invention, though it is needless to say that the present invention is not limited to them. These Examples are preceded by Preparative Examples for starting compounds. For the sake of convenience, some compounds of the present invention are described as Preparative Examples, which does not limit the present invention.

Preparative Example 1

4-Cyanophthalimide

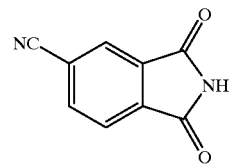

4-Aminophthalimide (40.0 g) was suspended in 300 ml of water, followed by the addition of 57 ml of concentrated hydrochloric acid. The obtained suspension was stirred under cooling with ice. A solution of 20.6 g of sodium nitrite in 69 ml of water was dropped into the above suspension at a bulk temperature of 5° C. or below.

The obtained mixture was cooled to −20° C., followed by the addition of 300 ml of toluene. The resulting mixture was adjusted to pH7 with sodium hydrogencarbonate under vigorous stirring to form a diazonium salt.

Separately, a solution of 105.7 g of potassium cyanide in 206 ml of water was dropped into a suspension of 63.4 g of cuprous chloride in 250 ml of water, while the suspension was vigorously stirred under cooling with ice. The obtained mixture was further stirred under cooling with ice for one hour, followed by the addition of 500 ml of ethyl acetate. The diazonium salt prepared above was added into the resulting mixture in several portions and the obtained mixture was stirred under cooling with ice for one hour.

The resulting mixture was filtered through Celite to remove insolubles and the Celite was washed with an ethyl acetate/tetrahydrofuran mixture. The filtrates were together left standing to cause liquid-liquid separation. The organic phase was washed with a saturated aqueous solution of sodium hydrogen-carbonate, dilute hydrochloric acid and a saturated aqueous solution of common salt, dried over anhydrous magnesium sulfate and freed from the solvent by vacuum distillation. The title compound (41 g) was obtained as a reddish-brown solid.

M.p.: 237.0–238.0° C.

MASS: 173 (MH+)

1H-NMR (400 MHz, DMSO-d6) δ: 8.00(1H, dd, J=7.5, 1.0 Hz), 8.29(1H, dd, J=7.5, 1.5 Hz), 8.36(1H, dd, J=1.5, 1.0 Hz), 11.73(1H, s)

Preparative Example 2

6-Cyano-2,3-dihydro-1,4-phthalazinedione

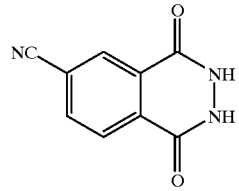

4-Cyanophthalimide (80 g) was suspended in 1000 ml of ethanol, followed by the addition of 25 ml of hydrazine monohydrate. The obtained mixture was stirred at room temperature for 5 hours.

The resulting mixture was concentrated in a vacuum to about one-half its original volume, followed by the addition of 1000 ml of water. The obtained mixture was acidified with dilute hydrochloric acid to precipitate crystals, which were recovered by filtration to give 71 g of the title compound as a brown powder.

1H-NMR (400 MHz, DMSO-d6) δ: 8.19(1H, brs), 8.27 (1H, dd, J=8.0, 1.0 Hz), 8.48(1H, brs), 11.39(2H, brs)

Preparative Example 3

6-Cyano-1,4-dichlorophthalazine

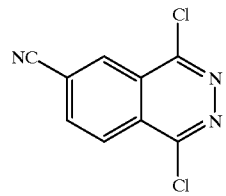

6-Cyano-2,3-dihydro-1,4-phthalazinedione (69 g) was suspended in 400 ml of phosphorus oxychloride, followed by the addition of 75 ml of diisopropylethylamine. The obtained mixture was heated under reflux for 40 minutes.

Excess phosphorus oxychloride was distilled away in a vacuum and the residue was dissolved in methylene chloride. The obtained solution was poured onto ice/water. The resulting mixture was filtered through Celite to remove insolubles and the Celite was washed weith methylene chloride. The filtrates were together extracted with methylene chloride and the organic phase was washed with a saturated aqueous solution of sodium hydrogencarbonate, dilute hydrochloric acid and a saturated aqueous solution of common salt, dried over anhydrous magnesium sulfate and filtered through silica gel. The filtrate was distilled in a vacuum to remove the solvent. The title compound (66 g) was obtained as a palely yellowish-orange solid.

1H-NMR (400 MHz, CDCl3) δ: 8.24(1H, dd, J=8.5, 1.5 Hz), 8.47(1H, dd, J=8.5, 1.0 Hz), 8.68(1H, dd, J=1.5, 1.0 Hz)

Preparative Example 4

4-Carbamoylphthalimide

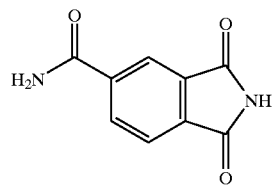

A solution of 21.1 g (0.10 mol) of trimellitoyl chloride in 25 ml of acetone was dropped into 200 ml of 29% aqueous ammonia, while the aqueous ammonia was stirred under cooling with ice. The resulting mixture was as such stirred for one hour, deaerated in a vacuum and acidified with concentrated hydrochloric acid under cooling with ice. The crystals thus precipitated were recovered by filtration, washed with water and dried with hot air to give 18.5 g of a mixture of 2,4-dicarbamoylbenzoic acid and 2,5-dicarbamoylbenzoic acid as a white crystal (yield: 89%).

This mixture (16.0 g, 0.077 mol) was suspended in 80 ml of N-methyl-2-pyrrolidinone. The obtained suspension was stirred under heating at 150° C. for 3 hours and cooled by allowing to stand, followed by the addition of 200 ml of water. The crystals thus precipitated were recovered by filtration, washed with water and dried with hot air. The title compound (13.3 g) was obtained as a light brown crystal (yield: 91%).

1H-NMR (400 MHz, DMSO-d6) δ: 7.70(1H, br s), 7.90 (1H, dd, J=7.2, 1.2 Hz), 8.28–8.31(2H, m), 8.32(1H, br s), 11.48(1H, br s)

Preparative Example 5

6-Carbamoyl-2,3-dihydro-1,4-phthalazinedione

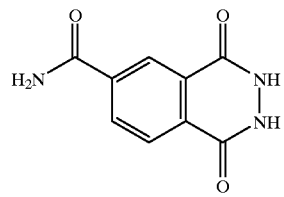

4-Carbamoylphthalimide (2.00 g, 0.011 mol) was suspended in 12 ml of N-methyl-2-pyrrolidinone, followed by the dropwise addition of 0.8 ml of hydrazine hydrate. The obtained mixture was stirred at room temperature for 30 minutes, followed by the addition of 5.5 ml of 3N hydrochloric acid and 50 ml of water. The crystals thus precipitated were recovered by filtration, washed with water and dried with hot air. The title compound (2.0 g) was obtained as a light brown crystal (yield: 94%).

1H-NMR (400 MHz, DMSO-d6) δ: 7.68(1H, br s), 8.12 (1H, br d, J=8.4 Hz), 8.32(1H, dd, J=8.4, 1.6 Hz), 8.39(1H, br s), 8.59(1H, br s), 11.69(2H, br s)

Preparative Example 6

6-Cyano-1,4-dichlorophthalazine

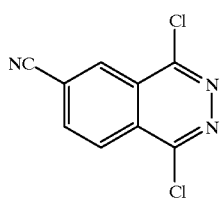

6-Carbamoyl-2,3-dihydro-1,4-phthalazinedione (1.00 g, 0.0049 mol) was suspended in a mixture comprising 20 ml of phosphorus oxychloride and 20 ml of thionyl chloride. The obtained suspension was heated under reflux one whole day and night and distilled in a vacuum to remove the solvent. The obtained residue was dissolved in methylene chloride, followed by washing with water. The organic phase was dried over anhydrous magnesium sulfate and purified by silica gel column chromatography to give 0.76 g of the title compound as a light brown crystal (yield: 70%).

Preparative Example 7

1,4,6-Trichlorophthalazine

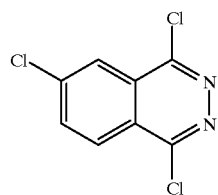

The title compound was prepared from 6-cyano-2,3-dihydro-1,4-phthalazinedione in a similar manner to that of Preparative Example 3.

1H-NMR (400 MHz, CDCl3) δ: 8.01(1H, dd, J=9.0, 2.0 Hz), 8.29(1H, d, J=9.0 Hz), 8.31(1H, d, J=2.0 Hz)

Preparative Example 8

1,4-Dichloro-6-nitrophthalazine

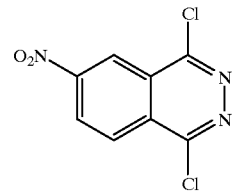

The title compound was prepared from 2,3-dihydro-6-nitro-1,4-phthalazinedione in a similar manner to that of Preparative Example 3.

1H-NMR (400 MHz, CDCl3) δ: 8.02(1H, dd, J=9.0, 0.5 Hz), 8.83(1H, dd, J=9.0, 2.0 Hz), 9.20(1H, dd, J=2.0, 0.5 Hz)

Preparative Example 9

5-Chloro-3-(pyrid-3-yl)methylenephthalide

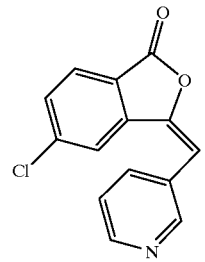

A mixture comprising 5.0 g of 4-chlorophthalic anhydride, 5.5 g of 3-pyridylacetic acid hydrochloride and 0.5 g of anhydrous sodium acetate was stirred without any solvent at 200° C. for 10 minutes.

Ethanol (100 ml) was added to the reaction mixture and the mixture thus obtained was cooled with ice to precipitate crystals, which were recovered by filtration to give 2.68 g of the title compound as a yellowish-orange crystal.

1H-NMR (400 MHz, DMSO-d6) δ: 7.24(1H, s), 7.79(1H, dd, J=8.0, 2.0 Hz), 7.89(1H, dd, J=8.0, 5.5 Hz), 8.03(1H, dd, J=8.0, 0.5 Hz), 8.35(1H, dd, J=2.0, 1.5 Hz), 8.56(1H, ddd, J=8.0, 2.0, 0.54 Hz), 8.74(1H, dd, J=5.5, 1.5), 9.00(1H, d, J=2.0)

Preparative Example 10

6-Chloro-4-(3-pyridylmethyl)-1(2H)-phthalazinone

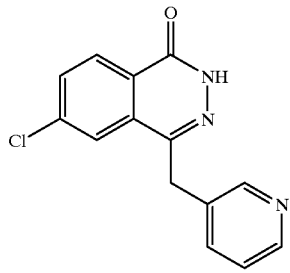

5-Chloro-3-(pyrid-3-yl)methylenephthalide (2.68 g) was dissolved in 100 ml of ethanol, followed by the addition of 2.0 ml of hydrazine monohydrate. The obtained mixture was heated under reflux for 4 hours, followed by the addition of 200 ml of water. The resulting mixture was neutralized with dilute hydrochloric acid to precipitate crystals, which were recovered by filtration to give 1.87 g of the title compound as a yellow powder.

1H-NMR (400 MHz, DMSO-d6) δ: 4.37(2H, s), 7.33(1H, ddd, J=8.5, 4.5, 1.0 Hz), 7.67–7.70(1H, m), 7.89(1H, dd, J=8.0, 2.0 Hz), 8.11(1H, d, J=2.0 Hz), 8.26(1H, d, J=8.5 Hz), 8.44(1H, dd, J=4.5, 1.5), 8.58–8.59(1H, m), 12.68(1H, s)

Preparative Example 11

1,6-Dichloro-4-(3-pyridylmethyl)phthalazine

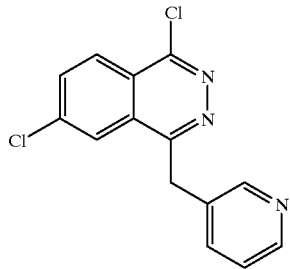

6-Chloro-4-(3-pyridylmethyl)-1(2H)-phthalazinone (0.86 g) was suspended in 10 ml of phosphorus oxychloride. The obtained suspension was heated under reflux for 2 hours and freed from the phosphorus oxychloride by vacuum distillation. The residue was dissolved in tetrahydrofuran. The obtained solution was neutralized with triethylamine, followed by the addition of water. The obtained mixture was extracted with ethyl acetate. The organic phase was washed with water and a saturated aqueous solution of common salt, dried over anhydrous magnesium sulfate and freed from the solvent by vacuum distillation. The residue was purified by silica gel column chromatography to give 0.49 g of the title compound as a pale yellow crystal.

1H-NMR (400 MHz, CDCl3) δ: 4.68(2H, s), 7.23(1H, dd, J=8.0, 4.5 Hz), 7.63(1H, ddd, J=8.0, 2.0, 1.5 Hz), 7.90(1H, dd, J=8.5, 2.0 Hz), 8.03(1H, d, J=2.0 Hz), 8.28(1H, d, J=8.5 Hz), 8.50(1H, dd, J=4.5, 1.5 Hz), 8.66(1H, d, J=2.0 Hz)

Preparative Example 12

4,6-Dichloro-1-(3-pyridylmethylphthalazine

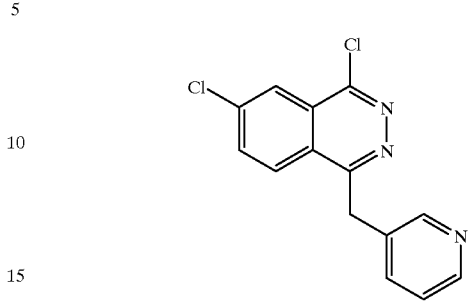

A mixture comprising 5.0 g of 4-chlorophthalic anhydride, 5.5 g of 3-pyridylacetic acid hydrochloride and 0.5 g of anhydrous sodium acetate was stirred without any solvent at 200° C. for 10 minutes.

Ethanol (100 ml) was added to the reaction mixture and the resulting mixture was cooled with ice to precipitate crystals, which were filtered out and the filtrate was concentrated in a vacuum. The obtained residue was subjected to silica gel column chromatography and the original-point fraction was removed. The effluent was concentrated in a vacuum and dissolved in 50 ml of ethanol, followed by the addition of 2.0 g of hydrazine monohydrate. The obtained mixture was heated under reflux for 6 hours.

The solvent was distilled away in a vacuum and dilute aqueous hydrochloric acid was added to the residue to form a solution. This solution was neutralized with a saturated aqueous solution of sodium hydrogencarboante and extracted with a chloroform/methanol mixture. The organic phase was dried over anhydrous magnesium sulfate and freed from the solvent by vacuum distillation. A mixture (2.27 g) comprising 7-chloro-4-(3-pyridylmethyl)-1(2H)-phthalazinone and 6-chloro-4-(3-pyridylmethyl)-1(2H)-phthalazinone was obtained as a light brown solid. This mixture (2.24 g, 8.25 mmol) was suspended in 20 ml of phosphorus oxychloride. The obtained suspension was heated under reflux for 2 hours and evaporated in a vacuum to dryness. The residue was dissolved in dichloromethane. The obtained solution was neutralized with a saturated aqueous solution of sodium carbonate and extracted with dichloromethane twice. The organic phases were combined, washed with water and a saturated aqueous solution of common salt, dried over magnesium sulfate and freed from the solvent by vacuum distillation to give 1.22 g of a crude product. This crude product was purified by silica gel column chromatography [dichloromethane/methanol (40:1)] to give 609 mg (2.10 mmol) of the title compound as a white crystal.

1H-NMR (400 MHz, CDCl3) δ: 4.71(2H, s), 7.20(1H, dd, J=8.0, 5.0 Hz), 7.60(1H, ddd, J=8.0, 2.0, 1.5 Hz), 7.86(1H, dd, J=8.5, 2.0 Hz), 8.06(1H, d, J=8.5 Hz), 8.27(1H, d, J=2.0 Hz), 8.47(1H, dd, J=5.0, 1.5 Hz), 8.65(1H, d, J=2.0 Hz)

Example 1

1-Chloro-4-(3-chloro-4-methoxybenzyl)amino-6-cyanophthalazine

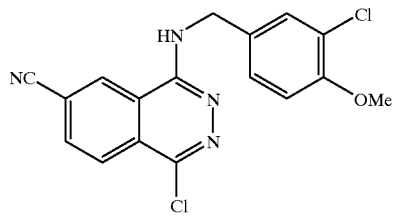

6-Cyano-1,4-dichlorophthalazine (66.2 g) prepared in Preparative Example 3 and 3-chloro-4-methoxybenzylamine (92 g) were suspended in 1200 ml of tetrahydrofuran, followed by the addition of 250 ml of triethylamine. The obtained mixture was heated under reflux for 6 hours.

The crystals thus precipitated were filtered out and the filtrate was concentrated in a vacuum. The residue was purified by silica gel column chromatography [solvent: toluene/tetrahydrofuran (10:1)] to recover a less polar product. The title compound (59 g) was obtained as a pale-yellow crystal.

M.p.: 213.0–214.5° C.

MASS: 359 (MH+)

1H-NMR (400 MHz, CDCl3) δ: 3.87(3H, s), 4.78(2H, d, J=5.0 Hz), 5.75(1H, t, J=5.0 Hz), 6.87(1H, d, J=8.5 Hz), 7.31(1H, dd, J=8.5, 2.0 Hz), 7.43(1H, d, J=2.0 Hz), 8.05(1H, dd, J=8.5, 1.5 Hz), 8.24(1H, dd, J=1.5, 1.0 Hz), 8.29(1H, dd, J=8.5, 0.5 Hz)

Example 2

4-Chloro-1-(3-chloro-4-methoxybenzyl)amino-6-cyanophthalazine

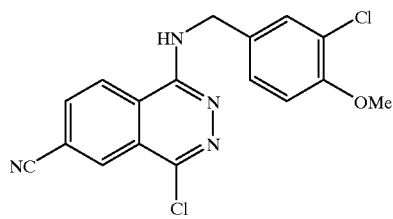

A more polar product prepared by repeating the same procedure as that of Example 1 was recovered to give 27 g of the title compound as a white crystal.

M.p.: 122.0–123.5° C.

MASS: 359 (MH+)

1H-NMR (400 MHz, CDCl3) δ: 3.91(3H, s), 4.80(2H, d, J=5.5 Hz), 5.43(1H, t, J=5.5 Hz), 6.92(1H, d, J=8.5 Hz), 7.33(1H, dd, J=8.5, 2.0 Hz), 7.45(1H, d, J=2.0 Hz), 7.89(1H, dd, J=8.5, 0.5 Hz), 8.03(1H, dd, J=8.5, 1.5 Hz), 8.55(1H, dd, J=1.5, 0.5 Hz)

Example 3

4-(3-Chloro-4-methoxybenzyl)amino-6-cyano-1-(4-hydroxypiperidino)phthalazine

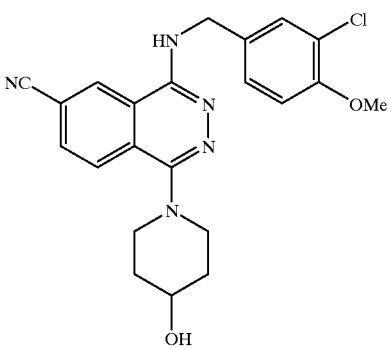

1-Chloro-4-(3-chloro-4-methoxybenzyl)amino-6-cyanophthalazine (10.0 g) prepared in Example 1 was dissolved in 50 ml of N-methyl-2-pyrrolidinone, followed by the addition of 43.32 g of 4-hydroxypiperidine- and 10 ml of diisopropylethylamine. The obtained mixture was heated at 170° C. for 8 hours.

Ethyl acetate was added to the reaction mixture and the obtained mixture was washed with water three times and with a saturated aqueous solution of common salt once, dried over anhydrous magnesium sulfate and freed from the solvent by vacuum distillation. The residue was purified by silica gel column chromatography [solvent: methylene chloride/methanol (30:1)] to give 10.1 g of the title compound as a yellow crystal.

M.p.: 172.0–173.5° C.

MASS: 424 (MH+)

1H-NMR (400 MHz, CDCl3) δ: 1.70(1H, brs), 1.80–1.90 (2H, m), 2.07–2.15(2H, m), 3.05–3.15(2H, m), 3.50–3.60 (2H, m), 3.87(3H, s), 3.90–4.00(1H, m), 4.74(2H, d, J=5.0 Hz), 5.41(1H, t, J=5.0 Hz), 6.87(1H, d, J=8.5 Hz), 7.29(1H, dd, J=8.5, 2.0 Hz), 7.42(1H, d, J=2.0 Hz), 7.95(1H, dd, J=8.5, 1.5 Hz), 8.12(1H, d, J=8.5 Hz), 8.21(1H, s)

Example 4

4-(3-Chloro-4-methoxybenzyl)amino-6-cyano-1-(4-hydroxypiperidino)phthalazine hydrochloride

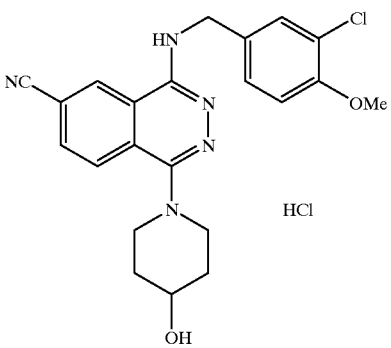

1-Chloro-4-(3-chloro-4-methoxybenzyl)amino-6-cyanophthalazine (10.0 g) prepared in Example 1 was dissolved in 50 ml of N-methyl-2-piperidone, followed by the addition of 43.32 g of 4-hydroxypyridine and 10 ml of diisopropylethylamine. The obtained mixture was heated at 170° C. for 8 hours.

Ethyl acetate was added to the reaction mixture. The obtained mixture was washed with water three times and with a saturated aqueous solution of common salt once, dried over anhydrous magnesium sulfate and freed from the solvent by vacuum distillation. The residue was purified by silica gel column chromatography [solvent: inethylene chloride/methanol (30:1)] to give 10.1 g of 4-(3-chloro-4-methoxybenzyl)amino-6-cyano-1-(4-hydroxypiperidino) phthalazine as a yellow crystal. This product (10.8 g) was suspended in a mixture comprising 60 ml of ethanol and 30 ml of water, followed by the addition of 30 ml of 1N aqueous hydrochloric acid. The obtained mixture was dissolved by heating and cooled by allowing to stand at room temperature.

The crystals thus precipitated were recovered by filtration and dried with hot air at 80° C. overnight to give 9.37 g of the title compound as a yellow crystal.

M.p.: 217–227 (dec.) °C.

MASS: 424 (MH+)

1H-NMR (400 MHz, DMSO-d6) δ: 1.61–1.70(2H, m), 1.90–1.97(2H, m), 2.97–3.04(2H, m), 3.37–3.48(2H, m), 3.70–3.79(1H, m), 3.84(3H, s), 4.70(2H, d, J=5.5 Hz), 7.15(1H, d, J=8.5 Hz), 7.44(1H, dd, J=8.5, 2.0 Hz), 7.59(1H, d, J=2.0 Hz), 8.23(1H, d, J=8.5 Hz), 8.45(1H, d, J=8.5 Hz), 9.33(1H, s), 10.10(1H, brs), 14.00(1H, brs)

Example 5

4-(3-Chloro-4-methoxybenzyl)amino-6-cyano-1-[4-oxo-1,4-dihydropyrid-1-yl)phthalazine

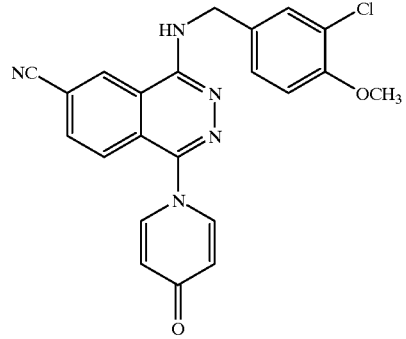

The title compound was prepared in a similar manner to that of Example 3.

M.p.: 218–219° C.

MASS: 418 (MH+)

1H-NMR (400 MHz, DMSO-d6) δ: 3.83(3H, s), 4.67(2H, d, J=5.6 Hz), 7.11(1H, d, J=8.4 Hz), 7.27(2H, dd, J=1.6 Hz, 4.4 Hz), 7.36(1H, dd, J=8.4, 2.0 Hz), 7.48(1H, d, J=2.0 Hz), 8.18–8.24(2H, m), 8.31(1H, dd, J=8.4, 1.2 Hz), 8.56(2H, dd, J=1.6 Hz, 4.4 Hz), 9.02(1H, d, J=1.2 Hz)

Example 6

4-(3-Chloro-4-methoxybenzyl)amino-6-cyano-1-[4-(hydroxymethyl)piperidino]phthalazine hydrochloride

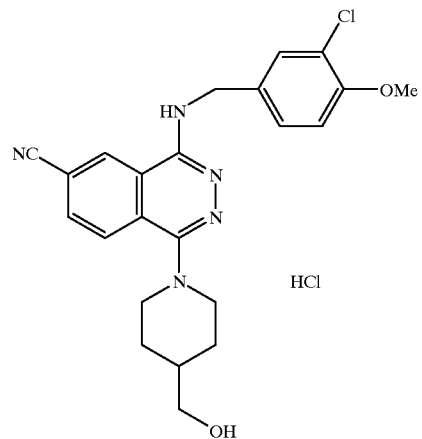

The title compound was prepared in a similar manner to that of Example 4.

MASS: 438 (MH+)

1H-NMR (400 MHz, DMSO-d6) δ: 1.40–1.50(2H, m), 1.61(1H, bs), 1.78–1.84(2H, m), 2.82–2.91(2H, m), 3.33 (2H, d, J=6.1 Hz), 3.52–3.62(2H, m), 3.83(3H, s), 4.71(2H, d, J=5.0 Hz), 7.14(1H, d, J=8.4 Hz), 7.45(1H, dd, J=8.4 Hz, 2.4 Hz), 7.61(1H, d, J=2.4 Hz), 8.21(1H, d, J=8.8 Hz), 8.46(1H, d, J=8.8 Hz), 9.42(1H, s)

Example 7

4-(3-Chloro-4-methoxybenzyl)amino-6-cyano-1-(3-hydroxypropyl)aminophthalazine

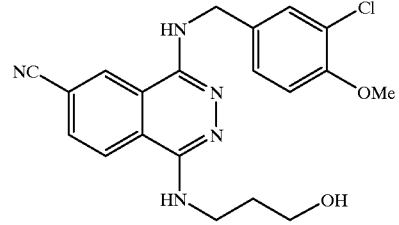

The title compound was prepared in a similar manner to that of Example 3.

M.p.: 132–135° C.

MASS: 398 (MH+)

1H-NMR (400 MHz, CDCl3) δ: 1.91–1.98(2H, m), 3.40 (1H, br s), 3.71–3.76(1H, m), 3.80(2H, t, J=5.6 Hz), 3.81 (2H, t, J=5.6 Hz), 3.91(3H, s), 4.68(2H, d, J=6.4 Hz), 5.30–5.34(1H, t, J=6.4 Hz), 6.92(1H, d, J=8.4 Hz), 7.32(1H, dd, J=8.4, 2.4 Hz), 7.46(1H, d, J=2.4 Hz), 7.85(1H, d, J=8.8 Hz), 7.95(1H, dd, J=8.8, 1.6 Hz), 8.10(1H, d, J=1.6 Hz)

Example 8

4-(3-Chloro-4-methoxybenzyl)amino-6-cyano-1-[4-(2-hydroxyethyl)piperidino]phthalazine hydrochloride

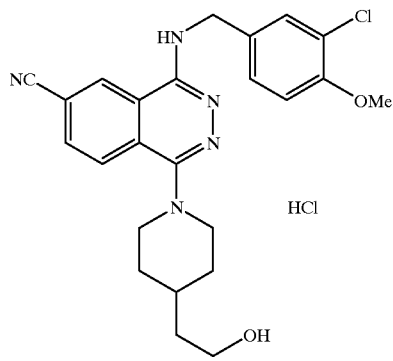

The title compound was prepared in a similar manner to that of Example 4

M.p.: 230 (dec.) °C.

MASS: 452 (MH+)

1H-NMR (400 MHz, DMSO-d6) δ: 1.39–1.53(4H, m), 1.65(1H, m), 1.82(2H, m), 2.87(2H, m), 3.50(2H, t, J=6.8 Hz), 3.56(2H, m), 3.85(3H, s), 4.74(2H, d, J=5.3 Hz), 7.15(1H, d, J=8.6 Hz), 7.49(1H, dd, J=8.6. 2.0 Hz), 7.63(1H, d, J=2.0 Hz), 8.23(1H, d, J=8.6 Hz), 8.47(1H, dd, J=8.6, 1.5 Hz), 9.53(1H, br s)

Example 9

4-(3-Chloro-4-methoxybenzyl)amino-6-cyano-1-(4-hydroxy-4-methylpiperidino)phthalazine hydrochloride

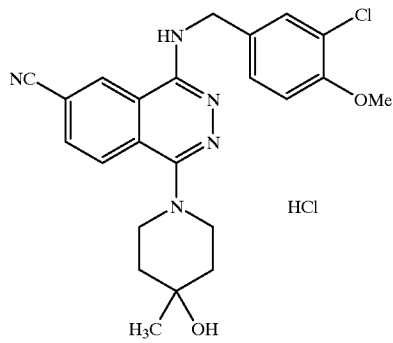

The title compound was prepared in a similar manner to that of Example 4.

M.p.: 230–240° C. (dec.)

MASS: 438 (MH+)

1H-NMR (400 MHz, DMSO-d6) δ: 1.22(3H, s), 1.61–1.71(2H, m), 1.73–1.84(2H, m), 3.18–3.33(4H, m), 3.85(3H, s), 4.76(2H, d, J=5.1 Hz), 7.15(1H, d, J=8.6 Hz), 7.51(1H, dd, J=8.6, 2.0 Hz), 7.66(1H, d, J=2.0 Hz), 8.23(1H, d, J=8.4 Hz), 8.46(1H, dd, J=8.4, 1.0 Hz). 9.63(1H, s)

Example 10

4-(3-Chloro-4-methoxybenzyl)amino-6-cyano-1-(3-hydroxypiperidino)phthalazine hydrochloride

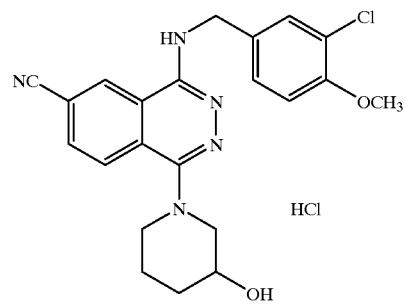

The title compound was prepared in a similar manner to that of Example 4.

M.p.: 189–199° C.

MASS: 424 (MH+)

1H-NMR (400 MHz, DMSO-d6) δ: 1.45(1H, m), 1.71 (1H, m), 1.84–1.97(2H, m), 2.86(1H, m), 2.98(1H, m), 3.32(1H, m), 3.42(1H, m), 3.83(1H, m), 3.85(3H, s), 4.76 (2H, d, J=5.7 Hz), 7.16(1H, d, J=8.6 Hz), 7.51(1H, dd, J=8.6, 2.0 Hz), 7.66(1H, d, J=2.0 Hz), 8.31(1H, d, J=8.4 Hz), 8.49(1H, dd, J=8.4, 1.3 Hz), 9.61(1H, s)

Example 11

4-(3-Chloro-4-methoxybenzyl)amino-6-cyano-1-(2-pyridylmethyl)aminophthalazine dihydrochloride

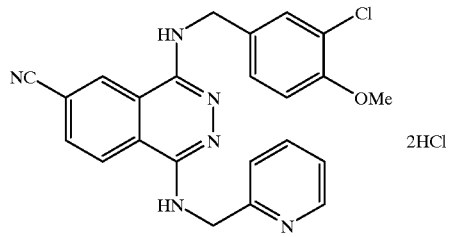

The title compound was prepared in a similar manner to that of Example 4.

M.p.: 188–190° C.

MASS: 431 (MH+)

1H-NMR (400 MHz, CD30D) δ: 3.83(3H, s), 4.62(2H, s), 5.05(2H, s), 7.08(1H, d, J=8.5 Hz), 7.35(1H, dd, J=8.5, 2.0 Hz), 7.47(1H, d, J=2.0 Hz), 7.98(1H, ddd, J=8.0, 6.0, 1.5 Hz), 8.16(1H, d, J=8.0 Hz), 8.48(1H, dd, J=8.5, 1.5 Hz), 8.57(1H, ddd, J=8.0, 8.0, 1.5 Hz), 8.62(1H, d, J=8.5 Hz), 8.76–8.78(1H, m), 9.06(1H, d, J=1.5 Hz)

Example 12

4-(3-Chloro-4-methoxybenzyl)amino-6-cyano-1-(4-pyridylmethyl)aminophthalazine dihydrochloride

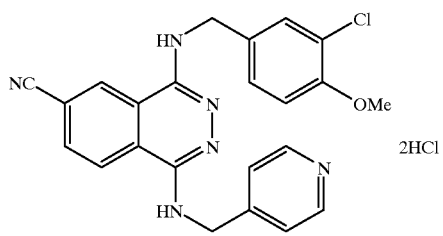

2HCl

The title compound was prepared in a similar manner to that of Example 4.

M.p.: 212–214° C.

MASS: 431 (MH+)

1H-NMR (400 MHz, CD30D) δ: 3.88(3H, s), 4.61(2H, s), 4.97(2H, s), 7.08(1H, d, J=8.5 Hz), 7.34(1H, dd, J=8.5, 2.0 Hz), 7.47(1H, d, J=2.0 Hz), 8.11–8.14(2H, m), 8.48(1H, dd, J=8.5, 1.5 Hz), 8.61(1H, d, J=8.5 Hz), 8.77–8.79(2H, m), 9.04(1H, d, J=1.5 Hz)

Example 13

4-(3-Chloro-4-methoxybenzyl)amino-6-cyano-1-(3-pyridylmethyl)aminophthalazine dihydrochloride

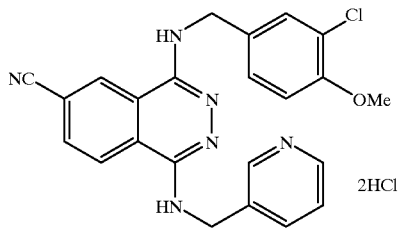

2HCl

The title compound was prepared in a similar manner to that of Example 4.

M.p.: 195.0–196.5° C.

MASS: 431 (MH+)

1H-NMR (400 MHz, DMSO-d6) δ: 3.84(3H, s), 4.59–4.63(2H, m), 4.78–4.82(2H, m), 7.12(1H, d, J=8.5 Hz), 7.40(1H, dd, J=8.5, 2.0 Hz), 7.55(1H, d, J=2.0 Hz), 7.92(1H, dd, J=8.0, 5.5 Hz), 8.46–8.52(1H, m), 8.58(1H, dd, J=8.5, 1.5 Hz), 8.77(1H, d, J=5.5 Hz), 8.82–8.92(1H, m), 8.93(1H, d, J=1.5 Hz), 9.36–9.42(1H, m)

Example 14

4-(3-Chloro-4-methoxybenzyl)amino-6-cyano-1-[N-(3-hydroxypropyl)-N-methylamino]phthalazine

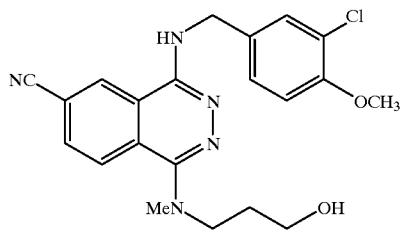

The title compound was prepared in a similar manner as that of Example 3.

M.p: amorphous

MASS: 412 (MH+)

1H-NMR (400 MHz, DMSO-d6) δ: 1.72–1.79(1H, m), 2.83(3H, s) 3.14–3.22(2H, m), 3.41–3.48(2H, m), 3.83(3H, s), 4.45(1H, t, J=4.8 Hz), 4.64(2H, d, J=5.6 Hz), 7.10(1H, d, J=8.0 Hz), 7.36(1H, dd, J=8, 2 Hz), 7.46(1H, d, J=2 Hz), 7.85(1H, t, J=5.6 Hz), 8.13–8.22(2H, m), 8.88(1H, d, J=1.2 Hz)

Example 15

4-(3-Chloro-4-methoxybenzyl)amino-6-cyano-1-[4-(2-pyridyl)piperazin-1-yl]phthalazine dihydrochloride

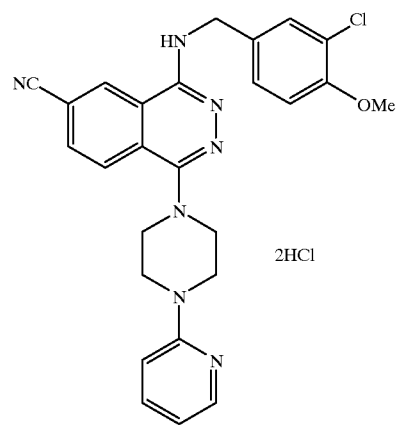

2HCl

The title compound was prepared in a similar manner to that of Example 4.

M.p.: 205–215 (dec.) °C.

MASS: 486 (MH+)

1H-NMR (400 MHz, CD30D) δ: 3.59(4H, m), 3.90(3H, s). 4.01(4H, m), 4.74(2H, s), 4.07(1H, m), 7.12(1H, d, J=8.6 Hz), 7.41(1H, dd, J=8.6, 2.4 Hz), 7.50(1H, d, J=9.2 Hz), 7.54(1H, d, J=2.4 Hz), 8.02(1H, m), 8.11(1H, m), 8.44(1H, dd, J=8.4, 1.6 Hz), 8.49(1H, dd, J=8.4, 0.8 Hz), 9.09(1H, dd, J=1.6, 0.8 Hz)

Example 16

4-(3-Chloro-4-methoxybenzyl)amino-6-cyano-1-[4-(2-pyrimidyl)piperazin-1-yl]phthalazine dihydrochloride

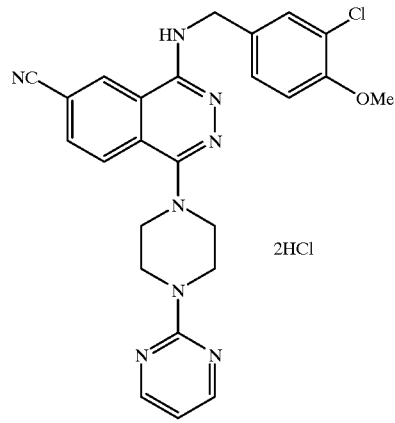

The title compound was prepared in a similar manner to that of Example 4.

M.p.: 205–209 (dec.) °C.

MASS: 487 (MH+)

1H-NMR (400 MHz, CD30D) δ: 3.52(4H, m), 3.90(3H, s), 4.17(4H, m), 4.73(2H, s), 6.94(1H, t, J=4.8 Hz), 7.12(1H, d, J=8.4 Hz), 7.41(1H, dd, J=8.4, 2.4 Hz), 7.54(1H, d, J=2.4 Hz), 8.43(1H, dd, J=8.4, 1.6 Hz), 8.49(1H, dd, J=8.4, 0.6 Hz), 8.57(2H, d, J=4.8 Hz), 9.08(1H, dd, J=1.6, 0.6 Hz)

Example 17

1-(4-Carbamoylpiperidino)-4-(3-chloro-4-methoxybenzyl)amino-6-cyanophthalazine

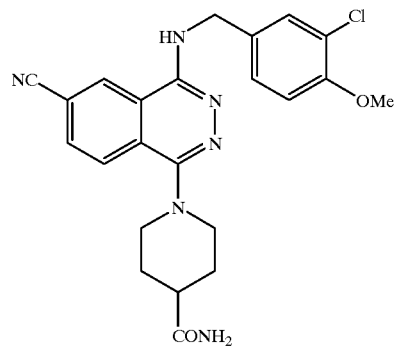

The title compound was prepared in a similar manner to that of Example 3.

M.p.: 228–230 (dec.)

MASS: 451 (MH+)

1H-NMR (400 MHz, DMSO-d6) δ: 1.80–1.95(4H, m), 2.30(1H, m), 2.82(2H, m), 3.44(2H, m), 3.82(3H, s), 4.64 (2H, d, J=5.8 Hz), 6.80(1H, br s), 7.10(1H, d, J=8.4 Hz), 7.32(1H, br s), 7.35(1H, dd, J=8.4, 2.0 Hz), 7.46(1H, d, J=2.0 Hz), 7.91(1H, t, J=5.8 Hz), 8.08(1H, d, J=8.8 Hz), 8.20(1H, dd, J=8.8, 1.2 Hz), 8.89(1H, d, J=1.2 Hz)

Example 18

4-(3-Chloro-4-methoxybenzyl)amino-6-cyano-1-[4-(2-hydroxyethyl)piperazin-1-yl]phthalazine dihydrochloride

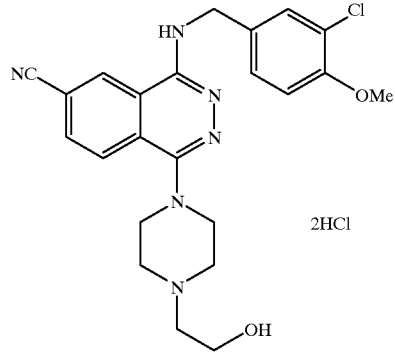

4-(3-Chloro-4-methoxybenzyl)amino-6-cyano-1-[4-(2-hydroxyethyl)piperazin-1-yl]phthalazine (12.0 g, 26.5 mmol) prepared in a similar manner to that of Example 3 was suspended in 600 ml of acetone, followed by the addition of 60 ml of 1N hydrochloric acid. The obtained mixture was stirred at room temperature for 30 minutes to precipitate crystals, which were recovered by filtration and dried at 90° C. for 6 hours to give 13.06 g of the title compound as a pale-yellow powder.

M.p.: 185–189° C.

MASS: 453 (MH+)

1H-NMR (400 MHz, DMSO-d6) δ: 3.25–3.31(2H, m), 3.37–3.52(5H, m), 3.60–3.70(4H, m), 3.85(3H, s), 3.86(2H, br t, J=5.7 Hz), 4.82(2H, d, J=5.7 Hz), 7.16(1H, d, J=8.8 Hz), 7.53(1H, dd, J=8.8, 2.0 Hz), 7.67(1H, d, J=2.0 Hz), 8.33(1H, d, J=8.4 Hz), 8.65(1H, dd, J=8.4, 1.1 Hz), 9.67(1H, s), 11.14(br, 1H)

Example 19

4-(3-Chloro-4-methoxybenzyl)amino-6-cyano-1-(4-oxopiperidino)phthalazine hydrochloride

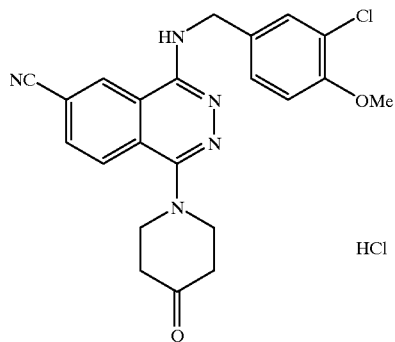

4-(3-Chloro-4-methoxybenzyl)amino-6-cyano-1-(4,4-ethylenedioxypiperidino)phthalazine (565 mg, 1.21 mmol) prepared in a similar manner to that of Example 3 was dissolved in 5 ml of trifluoroacetic acid. The obtained solution was stirred at room temperature for 18 hours and evaporated in a vacuum to dryness. The residue was dissolved in dichloromethane. The obtained solution was neutralized with a saturated aqueous solution of sodium hydrogencarbonate and extracted with dichloromethane twice. The organic phases were combined, washed with water and a saturated aqueous solution of common salt, dried over magnesium sulfate and freed from the solvent by vacuum distillation. The crude product thus obtained was purified by silica gel column chromatography [ethyl acetate/hexane (3:1)] to give 565 mg of a pale-yellow solid. This solid was recrystallized from 50% aqueous ethanol to give 423 mg (1.00 mmol) of 4-(3-chloro-4-methoxybenzyl)amino-6-cyano-1-(4-oxo-piperidino)phthalazine. This compound was convereted into a hydrochloride in the same manner as that employed in Example 4 for the formation of hydrochloride.

M.p.: 206° C. (dec.)

MASS: 422 (MH+)

1H-NMR (400 MHz, DMSO-d6) δ: 2.62–2.68(4H, m), 3.55–3.61(4H, m), 3.85(3H, s), 4.77(2H, d, J=5.5 Hz), 7.15(1H, d, J=8.5 Hz), 7.49(1H, dd, J=8.5, 2.0 Hz), 7.64(1H, d, J=2.0 Hz), 8.40(1H, d, J=8.5 Hz), 8.50(1H, dd, J=8.5, 1.5 Hz), 9.55(1H, d, J=1.5 Hz)

Example 20

1-(4-Carboxypiperidino)-4-(3-chloro-4-methoxybenzyl)-amino-6-cyanophthalazine hydrochloride

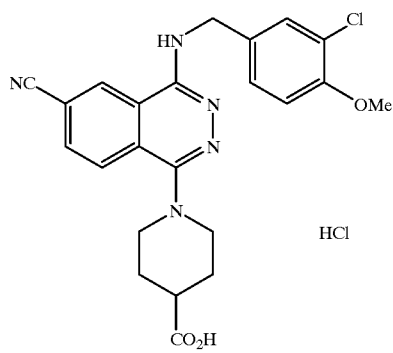

1-Chloro-4-(3-chloro-4-methoxybenzyl)amino-6-cyanophthalazine (2 g) prepared in Example 1 and t-butyl isonipecotate (2 g) were dissolved in 20 ml of N-methyl-2-pyrrolidone. The obtained solution was heated at 170° C. for 5 hours and cooled, followed by the addition of water. The obtained mixture was extracted with ethyl acetate. The organic phase was washed with water, dried over anhydrous magnesium sulfate and concentrated in a vacuum. The obtained residue was subjected to silica gel column chromatography and eluted with toluene/tetrahydrofuran (10:1) to give 1.6 g of 1-(4-tert-butoxycarbonyl-piperidino)-4-(3-chloro-4-methoxybenzyl)amino-6-cyanophthalazine.

1-(4-tert-Butoxycarbonylpiperidino-4-(3-chloro-4-methoxybenzyl)amino-6-cyanophthalazine (1.2 g) was stirred in 20 ml of formic acid at room temperature for 20 hours. The resulting mixture was concentrated in a vacuum and the obtained residue was subjected to silica gel column chromatography and eluted with dichloromethane/methanol (10:1) to give 1.05 g of the title compound.

M.p.: >270° C.

MASS: 452 (MH+)

1H-NMR (400 MHz, DMSO-d6) δ: 1.88–1.93(2H, m), 1.96–2.03(2H, m), 2.50–2.59(1H, m), 2.92–3.01(2H, m), 3.50–3.58(2H, m), 3.85(3H, s), 4.74(2H, d, J=5.2 Hz), 7.16(1H, d, J=8.4 Hz), 7.48(1H, dd, J=8.4, 2.4 Hz), 7.63 (11H, d, J=2.4 Hz), 8.26(1H, d, J=8.4 Hz), 8.46(1H, dd, J=8.4, 1.2 Hz), 9.49(1H, d, J=1.2 Hz)

Example 21

4-(3-Chloro-4-methoxybenzyl)amino-6-cyano-1 (2H)-phthalazinone

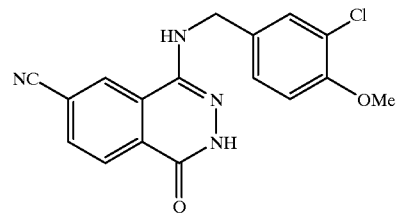

1-Chloro-4-(3-chloro-4-methoxybenzyl)amino-6-cyanophthalazine (1.0 g) prepared in Example 1 was dissolved in 10 ml of N-methyl-2-piperidone, followed by the addition of 0.26 ml of acetic acid and 2.1 ml of diisopropylethylamine. The obtained mixture was stirred at 170° C. for 7 hours, followed by the addition of 100 ml of water. The crystals thus precipitated were recovered by filtration.

The crystals were recrystallized from ethanol/water to give 0.6 g of the title compound as a yellow crystal.

M.p.: 292.5–294° C.

MASS: 341 (MH+)

1H-NMR (400 MHz, DMSO-d6) δ: 3.81(3H, s), 4.36(2H, d, J=5.5 Hz), 7.07(1H, d, J=8.5 Hz), 7.29(1H, dd.

J=8.5, 2.0 Hz), 7.30(1H, t, J=5.5 Hz), 7.41(1H, d, J=2.0 Hz), 8.19(1H, dd, J=8.0, 1.0 Hz), 8.32(1H, d, J=8.0 Hz), 8.73(1H, d, J=1.0 Hz), 11.86(1H, s)

Example 22

2-tert-Butoxycarbonylmethyl-4-(3-chloro-4-methoxybenzyl)amino-6-cyano-1(2H)-phthalazinone

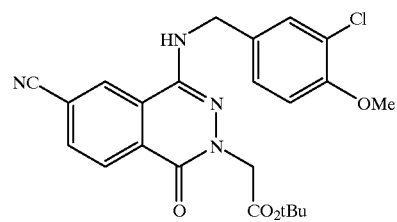

4-(3-Chloro-4-methoxybenzyl)amino-6-cyanol-1(2H)-phthalazinone (0.20 g) prepared in Example 21 was dissolved in 5 ml of N-methyl-2-pyrrolidinone, followed by the addition of 0.14 g of t-butyl bromoacetate and 0.24 g of potassium carbonate. The obtained mixture was stirred at 80° C. for 4 hours and poured into water, followed by extraction with ethyl acetate. The organic phase was washed with water twice and with a saturated aqueous solution of common salt, dried over anhydrous magnesium sulfate and freed from the solvent by vacuum distillation. The title compound (0.41 g) was obtained as a yellow crystal.

M.p.: 173.5–175° C.

MASS: 454 (MH+)

1H-NMR (400 MHz, DMSO-d6) δ: 1.49(9H, s), 3.90(3H, s), 4.37(2H, d, J=5.0 Hz), 4.91(2H, d, J=5.0 Hz), 6.90(1H, d, J=8.5 Hz), 7.25(1H, dd, J=8.5, 2.0 Hz), 7.42(1H, d, J=2.0 Hz), 7.93(1H, dd, J=8.0, 1.5 Hz), 8.00(1H, d, J=1.5 Hz), 8.53(1H, d, J=8.0 Hz)

Example 23

2-Carboxymethyl-4-(3-chloro-4-methoxybenzyl)amino-6-cyano-1(2H)-phthalazinone

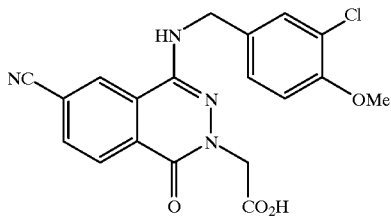

Trifluoroacetic acid (5 ml) was added to 0.41 g of the t-butyl ester prepared in Example 22. The obtained mixture was stirred at room temperature for one hour and freed from the trifluoroacetic acid by vacuum distillation. The obtained residue was recrystallized from ethanol/water to give 0.06 g of the title compound as a yellow crystal.

M.p.: 173–175° C.

MASS: 399 (MH+)

1H-NMR (400 MHz, DMSO-d6) δ: 3.81(3H, s), 4.34(2H, d, J=5.5 Hz), 4.62(2H, s), 7.06(1H, d, J=8.5 Hz), 7.32(1H, dd, J=8.5, 2.0 Hz), 7.43(1H, t, J=5.5 Hz), 7.45(1H, d, J=2.0 Hz), 8.22(1H, dd, J=8.0 Hz, 1.0 Hz), 8.34(1H, d, J=8.0 Hz), 8.74(1H, d, J=1.0 Hz), 12.95(1H, br s)

Example 24

4-(3-Chloro-4-methoxybenzyl)amino-6-cyano-2-[3-(tetrahydropyran-2-yloxy)propyl]-1(2H)-phthalazinone

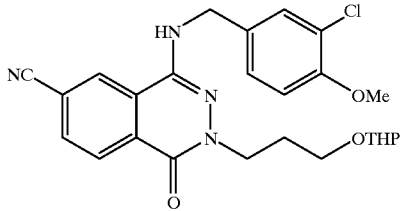

4-(3-Chloro-4-methoxybenzyl)amino-6-cyano-1(2H)-phthalazinone (0.20 g) prepared in Example 21 was dissolved in 5 ml of N-methyl-2-pyrrolidinone, followed by the addition of 0.24 g of 3-bromopropyl 2-tetrahydropyranyl ether and 0.24 g of potassium carbonate. The obtained mixture was stirred at 50° C. for 4 hours and poured into water, followed by extraction with ethyl acetate. The organic phase was washed with water twice and with a saturated aqueous solution of common salt, dried over anhydrous magnesium sulfate and freed from the solvent by vacuum distillation. The residue was purified by silica gel column chromatography [solvent: n-hexane/ethyl acetate (1:1)] to give 0.20 g of the title compound as a yellow crystal.

1H-NMR (400 MHz, CDCl3) δ: 1.44–1.83(6H, m), 2.08–2.17(2H, m), 3.45–3.51(2H, m), 3.81–3.87(2H, m), 3.89(3H, s), 4.17–4.30(2H, m), 4.46(2H, d, J=5.5 Hz), 4.57–4.59(1H, m), 5.02(1H, t, J=5.5 Hz), 6.90(1H, d, J=8.5 Hz), 7.28(1H, dd, J=8.5, 2.0 Hz), 7.44(1H, d, J=2.0 Hz), 7.93(1H, dd, J=8.0, 1.5 Hz), 8.06(1H, dd, J=1.5, 1.0 Hz), 8.55(1H, dd, J=8.0, 0.5 Hz)

Example 25

4-(3-Chloro-4-methoxybenzyl)amino-6-cyano-2-(3-hydroxypropyl)-1(2H)-phthalazinone

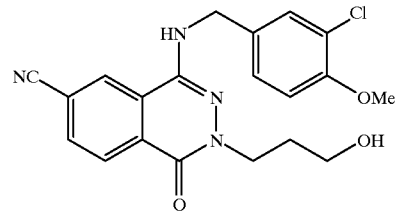

Methanol (20 ml) and 1N hydrochloric acid (2 ml) were added to the 4-(3-chloro-4-methoxybenzyl)amino-6-cyano-2-[3-(tetrahydropyran-2-yloxy)propyl]-1(2H)-phthalazinone (0.20 g) prepared in Example 24. The obtained mixture was stirred at room temperature for 3 hours.

The solvent was distilled away in a vacuum and the residue was recrystallized from ethanol/water to give 0.14 g of the title compound as a yellow crystal.

M.p.: 191.5–193.0° C.

MASS: 399 (MH+)

1H-NMR (400 MHz, DMSO-d6) δ: 1.79(2H, quint, J=6.0 Hz), 3.40(2H, q, J=6.0 Hz), 3.81(3H, s), 3.99(2H, t, J=6.0 Hz), 4.36(2H1, d, J=5.5 Hz), 7.07(1H, d, J=8.5 Hz), 7.33(1H, dd, J=8.5, 2.0 Hz), 7.45(1H, t, J=5.0 Hz), 7.46(1H, d, J=2.0 Hz), 8.19(1H, dd, J=8.0, 1.5 Hz), 8.34(1H, d, J=8.0 Hz), 8.71(1H, d, J=1.5 Hz)

Example 26

6-Cyano-1-(4-hydroxypiperidino)-4-(3,4-methylenedioxy-benzyl)aminophthalazine hydrochloride

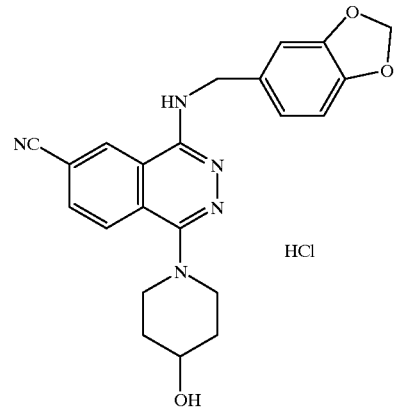

The title compound was prepared from 1-chloro-6-cyano-4-(3,4-methylenedioxybenzyl)aminophthalazine prepared in a similar manner to that of Example 1 in a similar manner to that of Example 4.

MASS: 404 (MH+)

1H-NMR (400 MHz, DMSO-d6) δ: 1.52–1.70(2H, m), 1.86–1.95(2H, m), 2.94–3.02(2H, m), 3.38–3.46(2H, m), 3.69–3.75(1H, m), 4.73(2H, d, J=5.0 Hz), 6.87(1H, d, J=8.0 Hz), 7.04(1H, dd, J=8, 1.6 Hz), 7.16(1H, d, J=1.6 Hz), 8.19(1H, d, J=8.4 Hz), 8.44(1H, d, J=8.4 Hz), 9.69(1H, s)

Example 27

4-(3-Chloro-4-methoxybenzyl)amino-1,6-dichlorophthalazine

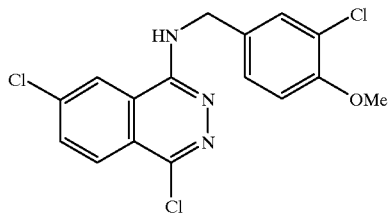

The title compound was prepared from 1,4,6-trichlorophthalazine prepared in Preparative Example 7 in a similar manner to that of Example 1.

M.p.: 197–198.5° C.

MASS: 368 (MH+)

1H-NMR (400 MHz, CDCl3) δ: 3.89(3H, s), 4.78(2H, d, J=5.5 Hz), 5.32(1H, t, J=5.5 Hz), 6.89(1H, d, J=8.5 Hz), 7.32(1H, dd, J=8.5, 2.0 Hz), 7.45(1H, d, J=2.0 Hz), 7.77(1H, d, J=2.0 Hz), 7.82(1H, dd, J=9.0, 2.0 Hz), 8.15(1H, d, J=9.0 Hz)

Example 28

1-(3-Chloro-4-methoxybenzyl)amino-4,6-dichlorophthalazine

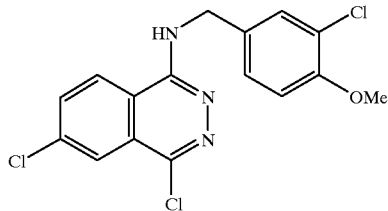

The title compound was prepared from 1,4,6-trichlorophthalazine prepared in Preparative Example 7 in a similar manner to that of Example 2.

M.p.: 168–169.5° C.

MASS:. 368 (MH+)

1H-NMR (400 MHz, CDCl3) δ: 3.90(3H, s), 4.78(2H, d, J=5.5 Hz), 5.30(1H, t, J=5.5 Hz), 6.91(1H, d, J=8.5 Hz), 7.33(1H, dd, J=8.5, 2.0 Hz), 7.45(1H, d, J=2.0 Hz), 7.72(1H, d, J=9.0 Hz), 7.78(1H, dd, J=9.0, 2.0 Hz), 8.18(1H, d, J=2.0 Hz)

Example 29

6-Chloro-4-(3-chloro-4-methoxybenzyl)amino-1-(3-hydroxypyrrolidino)phthalazine

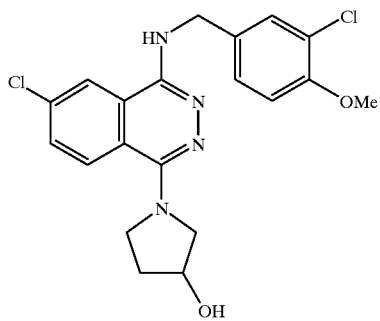

In a similar manner to that of Example 3, the title compound was prepared from 4-(3-chloro-4-methoxybenzyl)amino-1.6-dichlorophthalazine prepared in Example 27.

M.p.: 191–193° C.

MASS: 419 (MH+)

1H-NMR (400 MHz, CDCl3) δ: 2.01–2.08(1H, m), 2.14–2.24(1H, m), 3.56–3.64(1H, m), 3.73(1H, dt, J=14 Hz, 4 Hz), 3.82(1H, dd, J=6 Hz, 16 Hz), 3.88(3H, s), 3.94(1H, dt, J=14 Hz, 16 Hz), 4.58–4.62(1H, m), 4.69(2H, d, J=6 Hz), 4.83–4.90(1H, br t), 6.89(1H, d, J=8.4 Hz), 7.31(1H, dd, J=2.2 Hz, 8.4 Hz), 7.45(1H, d, J=2.2 Hz), 7.68(1H, dd, J=2.0 Hz, 8.8 Hz), 7.72(1H, d, J=2.0 Hz), 8.10(1H, d, J=8.8 Hz)

Example 30

(R)-6-Chloro-4-(3-chloro-4-methoxybenzyl)amino-1-[2-(hydroxymethyl)pyrrolidino]phthalazine hydrochloride

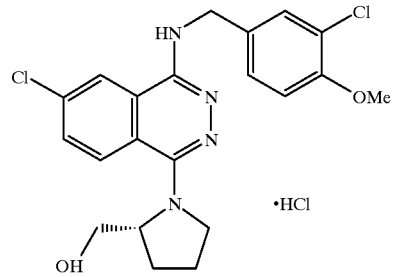

In a similar manner to that of Example 4, the title compound was prepared from 4-(3-chloro-4-methoxybenzyl)amino-1,6-dichlorophthalazine prepared in Example 27.

M.p.: 163–165° C.

MASS: 433 (MH+)

1H-NMR (400 MHz, CDCl3) δ: 1.80–1.95(1H, m), 1.95–2.04(1H, m), 2.15–2.24(1H, m), 3.42–3.48(1H, m), 3.75(1H, dd, J=16 Hz, 8 Hz), 3.86(1H, dd, J=6 Hz, 16 Hz), 3.90(3H, s), 3.90–3.97(1H, m), 4.70(2H, d, J=6 Hz), 4.70–4.77(1H, m), 4.83(1H, br, t, J=6 Hz), 6.91(1H, d, J=8.4 Hz), 7.31(1H, dd, J=8.4, 2.2 Hz), 7.45(1H, d, J=2.2 Hz), 7.69(1H, dd, J=8.4 Hz, 2.0 Hz), 7.72(1H, d, J=2.0 Hz), 8.08(1H, d, J=2.0 Hz)

Example 31

6-Chloro-4-(3-chloro-4-methoxybenzyl)amino-1-(imidazol-1-yl)phthalazine

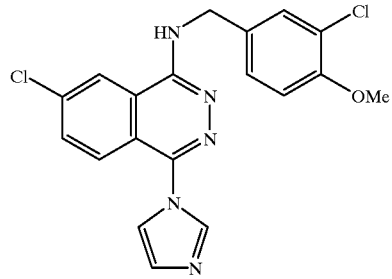

In a similar manner to that of Example 3, the title compound was prepared from 4-(3-chloro-4-methoxybenzyl)amino-1,6-dichlorophthalazine prepared in Example 27.

M.p.: 221–222.5° C.

1H-NMR (400 MHz, CDCl3) δ: 3.91(3H, s), 4.86(2H, d, J=5.5 Hz), 5.56(1H, t, J=5.5 Hz), 6.93(1H, d, J=8.5 Hz), 7.31(1H, br s), 7.36(1H, dd, J=8.5, 2.0 Hz), 7.41–7.42(1H, m), 7.48(1H, d, J=2.0 Hz), 7.67(1H, d, J=9.0 Hz), 7.81(1H, dd, J=9.0, 2.0 Hz), 7.99(1H, br s)

Example 32

6-Chloro-4-(3-chloro-4-methoxybenzyl)amino-1-(4-hydroxypiperidino)phthalazine hydrochloride

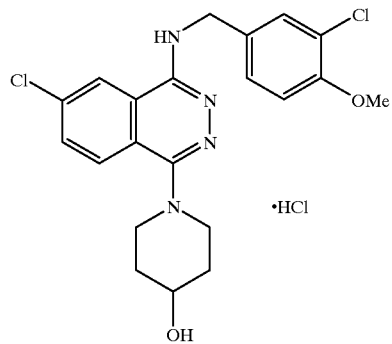

In a similar manner to that of Example 4, the title compound was prepared from 4-(3-chloro-4-methoxybenzyl)amino-1.6-dichlorophthalazine prepared in Example 27.

M.p.: 229–232 (dec.) ° C.

MASS: 433 (MH+)

1H-NMR (400 MHz, DMSO-d6) δ: 1.60–1.70(2H, m), 1.86–1.96(2H, m), 2.95–3.06(2H, m), 3.38–3.48(2H, m), 3.69–3.78(1H, m). 3.92(3H, s), 4.68(2H, d, J=4.6 Hz), 7.13(1H, d. J=8.8 Hz), 7.43(1H, d, J=8.8 Hz), 7.58(1H, s), 8.06–8.15(2H, m), 9.01(1H, s)

Example 33

1.6-Bis-(4-hydroxypiperidino)-4-(3-chloro-4-methoxybenzyl)aminophthalazine

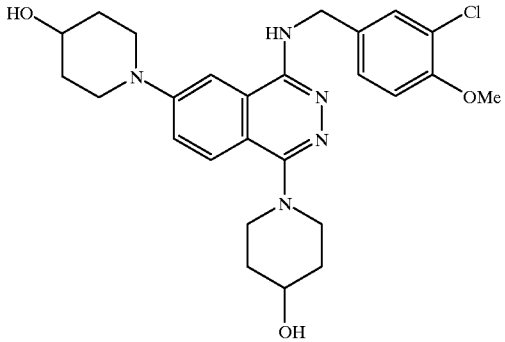

The title compound was prepared in a similar manner to that of Example 32 as a more polar product.

MASS: 498 (MH+)

1H-NMR (400 MHz, DMSO-d6) δ: 1.40–1.51(2H, m), 1.55–1.65(2H, m), 1.80–1.91(4H, m), 2.78–2.85(2H, m), 3.03–3.11(2H, m), 3.27–3.34(2H, m), 3.56–3.66(1H, m), 3.66–3.25(1H, m), 3.76–3.82(2H, m), 3.80(3H, s), 4.60(2H, d, J=5.3 Hz). 4.68(1H. d, J=4.1 Hz), 4.22(1H, d, J=4.1 Hz), 7.34(1H, d, J=8.6 Hz), 7.28(1H, dd, J=8.6 Hz, 2.0 Hz),

Example 34

6-Chloro-4-(3-chloro-4-methoxybenzyl)amino-1-morpholinophthalazine hydrochloride

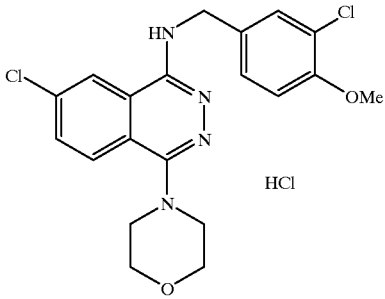

In a similar manner to that of Example 4, the title compound was prepared from 4-(3-chloro-4-methoxybenzyl)amino-1,6-dichlorophthalazine prepared in Example 27.

M.p.: 255–261 (dec.) ° C.

MASS: 419 (MH+)

1H-NMR (400 MHz, DMSO-d6) δ: 3.20–3.23(4H, m), 3.82–3.96(4H, m), 3.85(3H, s), 4.74(2H, d, J=6.0 Hz), 7.15(1H, d, J=8.8 Hz), 7.48(1H, dd, J=8.8, 2.0 Hz), 7.63(1H, d, J=2.0 Hz), 8.13(1H, dd, J=8.8, 2.0 Hz), 8.21(1H, d, J=8.8 Hz), 9.16(1H, d, J=2.0 Hz), 10.50(1H, br t), 13.97(1H, br s)

Example 35

6-Chloro-4-(3-chloro-4-methoxybenzyl)amino-1-(3-hydroxypropyl)aminophthalazine

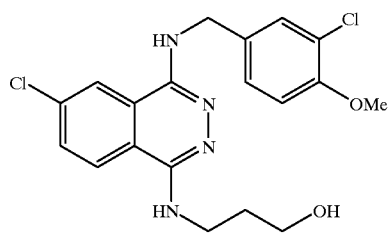

In a similar manner to that of Example 3, the title compound was prepared from 4-(3-chloro-4-methoxybenzyl)amino-1,6-dichlorophthalazine prepared in Example 27.

M.p.: 131–138° C.

MASS: 407 (MH+)

1H-NMR (400 MHz, CDCl3) δ: 1.83–1.94(2H, m), 3.75 (2H, t, J=5.4 Hz), 3.80(2H, t, J=5.4 Hz), 3.90(3H, s), 4.59(1H, br t, J=4.8 Hz), 4.66(2H, d, J=4.8 Hz), 5.14(1H, br t), 6.91(1H, d, J=8.4 Hz), 7.32(1H, dd, J=8.4, 2.4 Hz), 7.45(1H, d, J=2.4 Hz), 7.69(2H, s), 7.72(1H, d, J=1.6 Hz)

Example 36

6-Chloro-4-(3-chloro-4-methoxybenzyl)amino-1-[4-(hydroxymethyl)piperidino]phthalazine

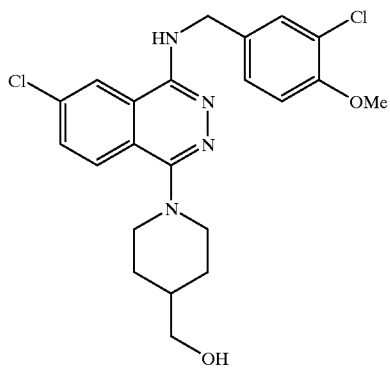

In a similar manner to that of Example 3, the title compound was prepared from 4-(3-chloro-4-methoxybenzyl)amino-1,6-dichlorophthalazine prepared in Example 27.

M.p.: 128–131° C.

MASS: 447 (MH+)

1H-NMR (400 MHz, CDCl3) δ: 1.48–1.63(3H, m), 1.76 (1H, m), 1.92(2H, m), 3.01(2H, dt, J=12.3, 2.0 Hz), 3.59–3.67(4H, m), 3.89(3H, s), 4.74(2H, d, J=5.1 Hz), 4.99(1H, br t, J=5.1 Hz), 6.89(1H, d, J=8.4 Hz), 7.32(1H, dd, J=8.4, 2.2 Hz), 7.45(1H, d, J=2.2 Hz), 7.70(11H, dd, J=8.6, 1.8 Hz), 7.73(1H, d, J=1.8 Hz), 7.99(1H, d, J=8.6 Hz)

Example 37

6-Chloro-4-(3-chloro-4-methoxybenzyl)amino-1-[4-(2-hydroxyethyl)piperidino]phthalazine

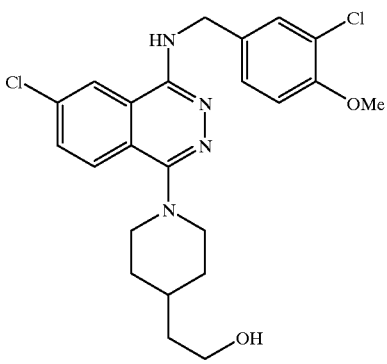

In a similar manner to that of Example 3, the title compound was prepared from 4-(3-chloro-4-methoxybenzyl)amino-1,6-dichlorophthalazine prepared in Example 27.

M.p.: 153–155° C.

MASS: 461 (MH+)

1H-NMR (400 MHz, CDCl3) δ: 1.41(br s), 1.54(2H, m), 1.60–1.76(3H, m), 1.88(2H, m), 2.98(2H, dt, J=12.5, 1.8 Hz), 3.59(2H, m), 3.78(2H, br t, J=6.2 Hz), 3.89(3H, s), 4.74(2H, d, J=5.3 Hz), 5.00(1H, br t, J=5.3 Hz), 6.89(1H, d, J=8.4 Hz), 7.31(1H, dd, J=8.4, 2.2 Hz), 7.45(1H, d, J=2.2 Hz), 7.69(1H, dd, J=8.8, 2.0 Hz), 7.73(1H, d, J=2.2 Hz), 7.98(1H, d, J=8.8 Hz)

Example 38

6-Chloro-4-(3-chloro-4-methoxybenzyl)amino-1-ethoxyphthalazine

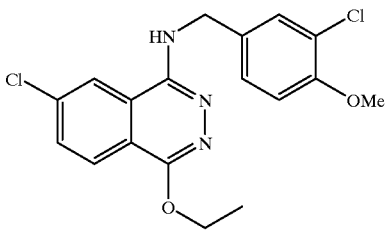

A solution of 120 mg of 60% oily sodium hydride in 20 ml of ethanol was added to 1.0 g of 4-(3-chloro-4-methoxybenzyl)amino-1,6-dichlorophthalazine prepared in Example 27. The obtained mixture was heated at 150° C. in a sealed tube overnight, cooled and concentrated in a vacuum. The residue was dissolved in ethyl acetate. The obtained solution was washed with water and a saturated aqueous solution of common salt, dried over anhydrous magnesium sulfate and concentrated in a vacuum. The obtained residue was subjected to silica gel column chromatography and eluted with dichloromethane/methanol (50:1) to give 0.9 g of the title compound.

M.p.: 111–115° C.

MASS: 387 (MH+)

1H-NMR (400 MHz, DMSO-d6) δ: 1.46(3H, t, J=7.2 Hz), 3.82(3H, s), 4.43(2H, q, J=7.2 Hz), 4.59(2H, d, J=5.6 Hz), 7.08(1H, d, J=8.4 Hz), 7.33(1H, dd, J=8.4, 2.0 Hz), 7.44(1H, d, J=2.0 Hz), 7.65(1H, t, J=5.6 Hz), 7.90(1H, dd, J=8.8, 2.0 Hz), 8.03(1H, d, J=8.8 Hz), 8.45(1H, d, J=2.0 Hz)

Example 39

6-Chloro-4-(3-chloro-4-methoxybenzyl)amino-1-(3-hydroxypropyloxy)phthalazine

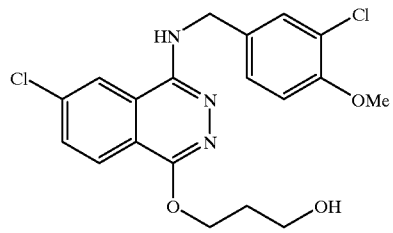

60% Sodium hydride (0.12 g, 3.0 mmol) was added to 8 ml of 1,3-propanediol. The obtained mixture was stirred at room temperature for one hour, followed by the addition of 1.0 g (2.7 mmol) of the compound prepared in Example 27. The obtained mixture was stirred at 150° C. for one hour, followed by the addition of water. The resulting mixture was extracted with ethyl acetate. The organic phase was washed with water and a saturated aqueous solution of common salt, dried over anhydrous magnesium sulfate and freed from the solvent by distillation. The residue was purified by silica gel column chromatography [solvent: dichloromethane/methanol (30:1)] and recrystallized from aqueous ethanol to give 0.58 g of the title compound as white needles.

M.p.: 124–126° C.

MASS: 408 (MH+)

1H-NMR (400 MHz, CDCl3) δ: 2.11(2H, quintet, J=8.0 Hz), 3.22(1H, br s), 3.82(2H, br), 3.87(3H, s), 4.67(2H, d, J=5.3 Hz), 4.70(2H, t, J=6.0 Hz), 5.08(1H, t, J=5.3 Hz), 6.85(1H, d, J=8.4 Hz), 7.28(1H, dd, J=8.4, 2.2 Hz), 7.42(1H, d, J=2.2 Hz), 7.69(1H, dd, J=8.8, 1.8 Hz), 7.75(1H, d, J=1.8 Hz), 8.05(1H, d, J=8.8 Hz)

Example 40

6-Chloro-4-(3-chloro-4-methoxybenzyl)amino-1-[N-(3-hydroxypropyl)-N-methylamino]phthalazine

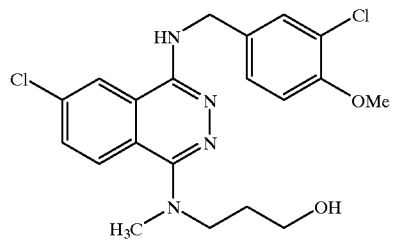

The compound (1.0 g, 2.7 mmol) prepared in Example 27 was dissolved in 9 ml of N-methyl-2-pyrrolidone, followed by the addition of 0.7 g (4.1 mmol) of N-methylpropanolamine hydrobromide and 1.14 g (8.2 mmol) of anhydrous potassium carbonate. The obtained mixture was stirred at 170° C. for 7.5 hours, followed by the addition of water. The resulting mixture was extracted with ethyl acetate. The organic phase was washed with water and a saturated aqueous solution of common salt, dried over anhydrous magnesium sulfate and freed from the solvent by distillation. The residue was purified by silica gel column chromatography [solvent: dichloromethane/methanol (20:1)] and crystallized from dichloromethane/ether to give 37 mg of the title compound as white needles.

M.p.: 115–117° C.

MASS: 421 (MH+)

1H-NMR (400 MHz, CDCl3) δ: 1.95(2H, quintet, J=6.0 Hz), 2.85(1H, br s), 2.99(3H, s), 3.51(2H, t, J=6.0 Hz), 3.75(2H, t, J=6.0 Hz), 3.90(3H, s), 4.74(2H, d, J=5.3 Hz), 4.95(1H, br), 6.91(1H, d, J=8.4 Hz), 7.33(1H, dd, J=8.4, 2.0 Hz), 7.46(1H, d, J=2.2 Hz), 7.72(1H, dd, J=9.3, 2.0 Hz), 7.72(1H, d, J=2.0 Hz), 8.05(1H, d, J=9.3 Hz)

Example 41

6-Chloro-4-(3-chloro-4-methoxybenzyl)amino-1-(4-oxopiperidino)phthalazine hydrochloride

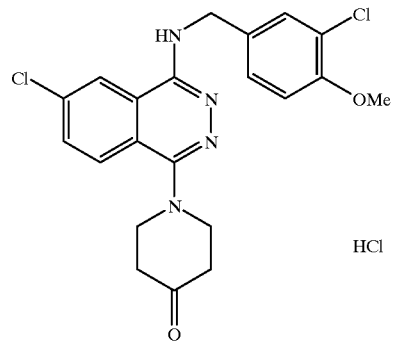

In a similar manner to that of Example 19, the title compound was prepared from the compound prepared in Example 27.

M.p.: 197 (dec.) ° C.

MASS: 431 (MH+)

1H-NMR (400 MHz, DMSO-d6) δ: 2.62–2.66(4H, m), 3.57–3.61(4H, m), 3.85(3H, s), 4.73(2H, d, J=6.0 Hz), 7.16(1H, d, J=8.5 Hz), 7.45(1H, dd, J=8.5, 2.0 Hz), 7.60(1H, d, J=2.0 Hz), 8.17(1H, dd, J=9.0, 2.0 Hz), 8.28(1H, d, J=9.0 Hz), 9.02(1H, br s)

Example 42

6-Chloro-4-(3-chloro-4-methoxybenzyl)amino-1-(4-ethoxycarbonylpiperidino)phthalazine

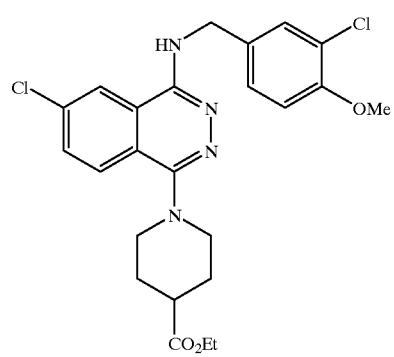

In a similar manner to that of Example 3, the title compound was prepared from the compound prepared in Example 27.

M.p.: 162–164.5° C.

MASS: 489 (MH+)

1H-NMR (400 MHz, CDCl3) δ: 1.29(3H, t, J=7.0 Hz), 1.96–2.14(4H, m), 2.50–2.58(1H, m), 2.99–3.07(2H, m), 3.57–3.63(2H, m), 3.91(3H, s), 4.19(2H, q, J=7.0 Hz), 4.75(2H, d, J=5.0 Hz), 4.92(1H, t, J=5.0 Hz), 6.91(1H, d, J=8.5 Hz), 7.32(1H, dd, J=8.5, 2.0 Hz), 7.46(1H, d, J=2.0 Hz), 7.70(1H, d, J=2.0 Hz), 7.71(1H, dd, J=8.0, 2.0 Hz), 7.99(1H, d, J=8.0 Hz)

Example 43

1-(4-Carboxypiperidino)-6-chloro-4-(3-chloro-4-methoxybenzyl)aminophthalazine

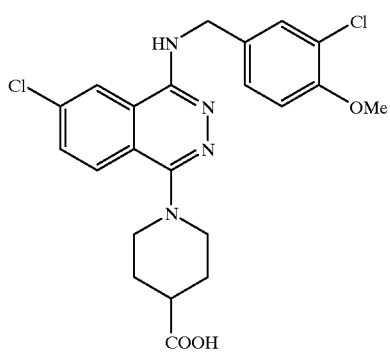

Methanol (50 ml), tetrahydrofuran (50 ml) and 1N aqueous solution (10 ml) of sodium hydroxide were added to 3.00 g of the compound prepared in Example 42. The obtained mixture was stirred at room temperature overnight and freed from the solvent by vacuum distillation. The residue was dissolved in 100 ml of water, followed by the addition of 10 ml of 1N hydrochloric acid. The crystals thus precipitated were recovered by filtration to give 2.76 g of the title compound as a pale-yellow crystal.

M.p.: 239.5–242° C. (dec.)

MASS: 489 (MH+)

1H-NMR (400 MHz, DMSO-d6) δ: 1.78–1.90(2H. m), 1.93–2.00(21, m), 2.40–2.50(1H, m), 2.83–2.90(2H, m), 3.35–3.45(2H, m), 3.82(3H, s), 4.61(2H, d, J=5.5 Hz), 7.09(1H, d, J=8.5 Hz), 7.33(1H, dd, J=8.5, 2.0 Hz), 7.43(1H, d, J=2.0 Hz), 7.75(1H, t, J=5.5 Hz), 7.88(1H, dd, J=9.0, 2.0 Hz), 7.98(1H, d, J=9.0 Hz), 8.44(1H, d, J=2.0 Hz)

Example 44

1-[N3-Carboxypropyl)-N-methylamino]-6-chloro-4-(3-chloro-4-methoxybenzyl)aminophthalazine

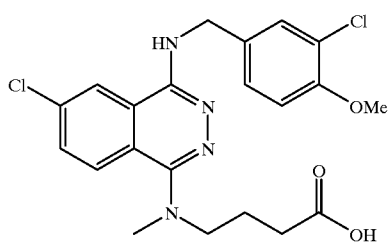

6-Chloro-1-[N-(3-ethoxycarbonylpropyl)-N-methylamino]-4-(3-chloro-4-methoxybenzyl)aminophthalazine was prepared from the compound prepared in Example 27 in a similar manner to that of Example 3 and further converted into the title compound in a similar manner to that of Example 43.

M.p.: 248–250 (dec.) ° C.

1H-NMR (400 MHz, DMSO-d6) δ: 1.76–1.86(1H, m), 2.06–2.14(1H, m), 2.80(3H, s), 3.06–3.14(2H, m), 3.81(3H, s), 4.59(2H, d, J=6 Hz), 7.08(1H, d, J=8.4 Hz), 7.34(1H, dd, J=8.4, 2.2 Hz), 7.44(1H, d, J=2.2 Hz), 7.86–7.95(2H, m), 8.02(1H, d, J=8.8 Hz), 8.54(1H, d, J=2.0 Hz)

Example 45

6-Chloro-1-(4-ethoxycarbonylpiperidino)-4-(3,4-methylenedioxybenzyl)aminophthalazine

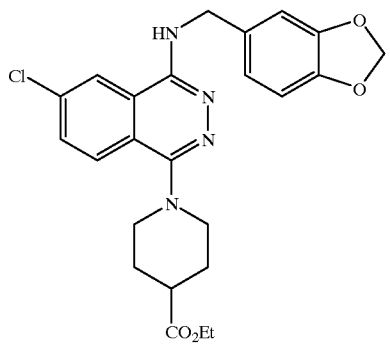

A mixture (4.83 g) comprising 1,6-dichloro-4-(3,4-methylenedioxybenzyl)aminophthalazine and 4,6-dichloro-1-(3,4-methylenedioxybenzyl)aminophthalazine was prepared from 1,4,6-trichlorophthalazine (3.38 g) prepared in Preparative Example 7 and piperonylamine (2.21 g) in a similar manner to that of Example 1. The title compound (0.22 g) was prepared from 0.8 g of the mixture in a similar manner to that of Example 3 as a less polar product.

1H-NMR (400 MHz, CDCl3) δ: 1.28(3H, t, J=7.0 Hz), 1.90–2.10(4H, m), 2.46–2.55(1H, m), 2.96–3.05(2H, m), 3.53–3.60(2H, m), 4.16(2H, q, J=7.0 Hz), 4.70(2H, d, J=5.0 Hz), 5.21(1H, t, J=5.0 Hz), 5.91(2H, s), 6.73(1H, d, J=8.0 Hz), 6.87(1H, dd, J=8.0, 1.5 Hz), 6.91(1H, d, J=1.5 Hz), 7.68(1H, dd, J=8.5, 2.0 Hz), 7.78(1H, d, J=2.0 Hz), 7.96(1H, d, J=8.5 Hz)

Example 46

6-Chloro-4-(4-ethoxycarbonylpiperidino)-1-(3,4-methylenedioxybenzyl)aminophthalazine

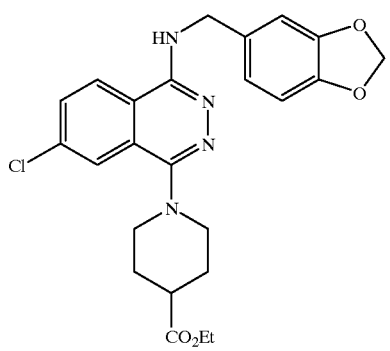

The title compound (0.21 g) was prepared by repeating the same procedure as that of Example 45 and recovering a more polar product.

1H-NMR (400 MHz, CDCl3) δ: 1.25(3H, t, J=7.0 Hz), 1.96–2.14(4H, m), 2.48–2.57(1H, m), 3.09–3.13(2H, m), 3.54–3.61(2H, m), 4.18(2H, q, J=7.0 Hz), 4.71(2H, d, J=5.0 Hz), 5.13(1H, t, J=5.0 Hz), 5.93(2H, s), 6.75(1H, d, J=8.0 Hz, 6.88(1H, dd, J=8.0, 1.5 Hz), 6.92(1H, d, J=1.5 Hz), 7.65(1H, dd, J=9.0, 2.0 Hz), 7.71(1H, d, J=9.0 Hz), 7.97(1H, d, J=2.0 Hz)

Example 47

1-(4-Carboxypiperidino)-6-chloro-4-(3,4-methylene-dioxybenzyl)aminophthalazine

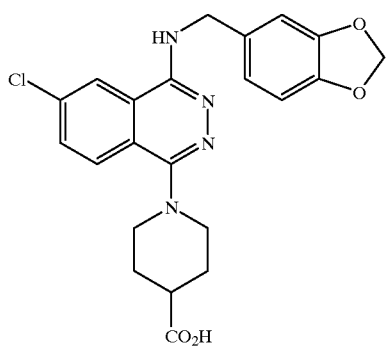

In a similar manner to that of Example 43, the title compound was prepared from the compound prepared in Example 45.

M.p.: 165–187° C.

MASS: 441 (MH+)

1H-NMR (400 MHz, DMSO-d6) δ: 1.80–1.91(2H, m), 1.94–2.01(2H, m), 2.43–2.52(1H, m), 2.86–2.94(2H, m), 3.40–3.50(2H, m), 4.61(2H, d, J=5.0 Hz), 5.98(2H, s), 6.87(1H, d, J=8.0 Hz), 6.90(1H, dd, J=8.0, 1.0 Hz), 7.00(1H, d, J=1.0 Hz), 7.95(1H, br d, J=9.0 Hz), 8.03(1H, d, J=9.0 Hz), 9.58(1H, br s)

Example 48

4-(4-Carboxypiperidino)-6-chloro-1-(3,4-methylene-dioxybenzyl)aminophthalazine

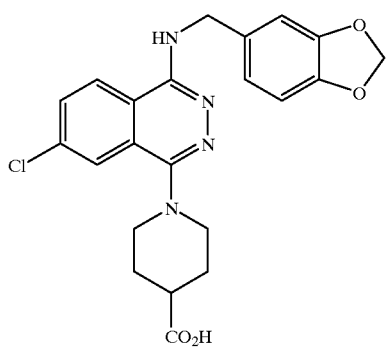

In a similar manner to that of Example 43, the title compound was prepared from the compound prepared in Example 46.

M.p.: 152–154° C.

MASS: 441 (MH+)

1H-NMR (400 MHz, DMSO-d6) δ: 1.80–1.90(2H, m), 1.94–2.01(2H, m), 2.41–2.50(1H, m), 2.85–2.92(2H, m), 3.35–3.43(2H, m), 4.62(2H, d, J=5.0 Hz), 5.96(2H, s), 6.84(1H, d, J=8.0 Hz), 6.88(1H, dd, J=8.0, 1.5 Hz), 6.97(1H, d, J=1.5 Hz), 7.89(1H, d, J=2.0 Hz), 7.96(1H, dd, J=9.0, 2.0 Hz), 8.39(1H, d, J=9.0 Hz)

Example 49

1-Chloro-4-(3-chloro-4-methoxybenzyl)amino-6-nitrophthalazine

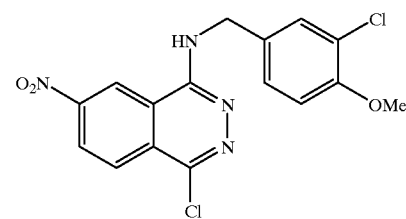

In a similar manner to that of Example 1, the title compound was prepared from 1,4-dichloro-6-nitrophthalazine prepared in Preparative Example 8.

M.p.: 217.0–217.5° C.

MASS: 379 (MH+)

1H-NMR (400 MHz, CDCl3) δ: 3.90(3H, s), 4.83(2H, d, J=5.5 Hz), 5.73(1H, t, J=5.5 Hz), 6.91(1H, d, J=8.0 Hz), 7.35(1H, dd, J=8.0, 2.0 Hz), 7.47(1H, d, J=2.0 Hz), 8.38(1H, d, J=9.0 Hz), 8.65(1H, dd, J=9.0, 2.0 Hz), 8.73(1H, d, J=2.0 Hz)

Example 50

4-Chloro-1-(3-chloro-4-methoxybenzyl)amino-6-nitrophthalazine

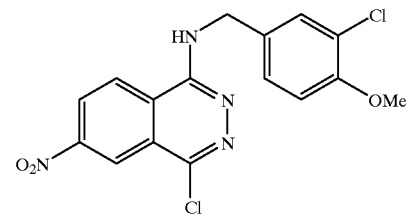

In a similar manner to that of Example 2, the title compound was prepared from 1,4-dichloro-6-nitrophthalazine prepared in Preparative Example 8.

M.p.: 179–180.5° C.

MASS: 379 (MH+)

1H-NMR (400 MHz, DMSO-d6) δ: 3.82(3H, s), 4.70(2H, d, J=5.6 Hz), 7.10(1H, d, J=8.4 Hz), 7.35(1H, d, J=8.8 Hz), 7.47(1H, d, J=2.0 Hz), 8.63(1H, t, J=5.6 Hz), 8.65(1H, d, J=8.8 Hz), 8.71(1H, d, J=2.4 Hz), 8.75(1H, dd, J=8.8, 2.4 Hz)

Example 51

4-(3-Chloro-4-methoxybenzyl)amino-1-(4-hydroxy-piperidino)-6-nitrophthalazine hydrochloride

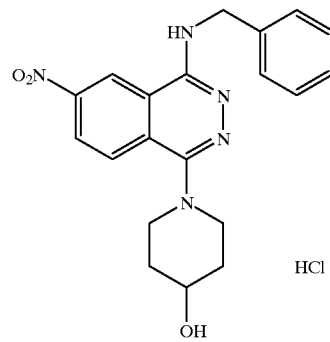

In a similar manner to that of Example 4, the title compound was prepared from the compound prepared in Example 49.

M.p.: 245–246 (dec.) ° C.

MASS: 444 (MH+)

1H-NMR (400 MHz, DMSO-d6) δ: 1.70(2H, m), 1.96 (2H, m), 3.05(2H, m), 3.48(2H, m), 3.77(1H, m), 3.86(3H, s), 4.78(2H, d, J=5.2 Hz), 7.17(1H, d, J=8.4 Hz), 7.48(1H, dd, J=8.4, 2.0 Hz), 7.63(1H, d. J=2.0 Hz), 8.34(1H, d, J=9.2 Hz), 8.78(1H, dd, J=9.2, 2.0 Hz), 9.78(1H, d, J=2.0 Hz), 10.59(1H, br s), 14.04(1H, br s)

Example 52

4-(3-Chloro-4-methoxybenzyl)amino-1-[4-(hydroxymethyl)piperidino]-6-nitrophthalazine hydrochloride

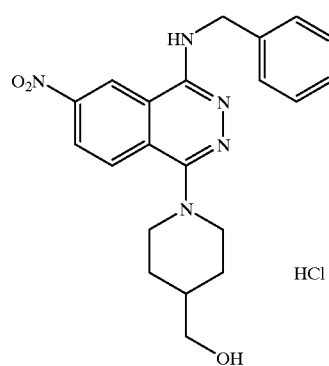

In a similar manner to that of Example 4, the title compound was prepared from the compound prepared in Example 49.

M.p.: 232–233 (dec.) ° C.

MASS: 458 (MH+)

1H-NMR (400 MHz, DMSO-d6) δ: 1.48(2H, m), 1.64 (1H, m), 1.83(2H, m), 2.90(2H, m), 3.37(2H, d, J=6.4 Hz), 3.61(2H,m), 3.85(3H, s), 4.77(2H, d, J=6.0 Hz), 7.17(1H, d, J=8.4 Hz), 7.48(1H, dd, J=8.4, 2.4 Hz), 7.63(1H, d. J=2.4 Hz), 8.32(1H, d, J=9.2 Hz), 8.78(1H, dd, J=9.2, 2.0 Hz), 9.77(1H, d, J=2.0 Hz), 10.56(1H, br s)

Example 53

4-(3-Chloro-4-methoxybenzyl)amino-1-[4-(2-hydroxyethyl)piperidino]-6-nitrophthalazine hydrochloride

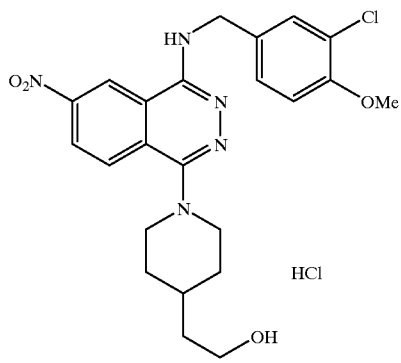

In a similar manner to that of Example 4, the title compound was prepared from the compound prepared in Example 49.

M.p.: 233–236 (dec.) ° C.

MASS: 472 (MH+)

1H-NMR (400 MHz, DMSO-d6) δ: 1.42–1.53(4H, m), 1.66(1H1, m), 1.84(2H, m), 2.89(2H, m), 3.51(2H, t, J=6.6 Hz), 3.58(2H, m), 3.85(3H, s), 4.76(2H, d, J=5.6 Hz), 7.17(1H, d, J=8.8 Hz), 7.47(1H, dd, J=8.8, 2.0 Hz), 7.62(1H, d, J=2.0 Hz), 8.33(1H, d, J=8.8 Hz), 8.77(1H, dd, J=8.8, 2.0 Hz), 9.74(1H, d, J=2.0 Hz), 10.45(1H, br s)

Example 54

4-(3-Chloro-4-methoxybenzyl)amino-1-[4-(2-hydroxyethyl)piperazin-1-yl]-6-nitrophthalazine

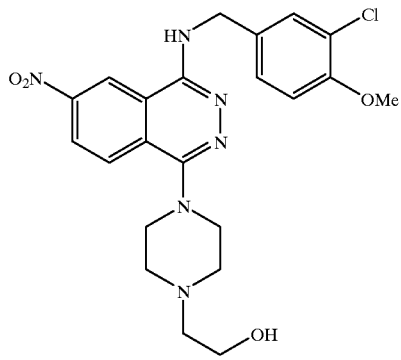

In a similar manner to that of Example 3, the title compound was prepared from the compound prepared in Example 49.

M.p.: 199–200 (dec.) ° C.

MASS: 473 (MH+)

1H-NMR (400 MHz, CDCl3) δ: 2.69(2H, t, J=5.4 Hz), 2.80(4H, br s), 3.37(4H, br t), 3.70(2H, t, J=5.4 Hz), 3.90(3H, s), 4.79(2H, d, J=5.2 Hz), 6.87(1H, t, J=5.2 Hz), 6.91(1H, d, J=8.4 Hz), 7.37(1H, dd, J=8.4, 2.4 Hz), 7.50(1H, d, J=2.4 Hz), 8.16(1H, d, J=9.2 Hz), 8.51(1H, dd, J=9.2, 2.0 Hz), 9.13(1H, d, J=2.0 Hz)

Example 55

1-(4-Ethoxycarbonylpiperidino)-4-(3-chloro-4-methoxybenzyl)amino-6-nitrophthalazine

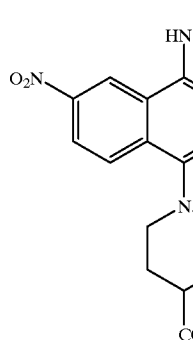

In a similar manner to that of Example 3, the title compound was prepared from the compound prepared in Example 49.

M.p.: 208.5–209.5° C.

MASS: 500 (MH+)

1H-NMR (400 MHz, CDCl3) δ: 1.30(3H, t, J=7.0 Hz), 2.01–2.15(4H, m), 2.53–2.59(1H, m), 3.04–3.11(2H, m), 3.56–3.64(2H, m), 3.92(3H. s), 4.20(2H, q, J=7.0 Hz), 4.79(2H, d, J=5.5 Hz), 5.23(1H, t, J=5.5 Hz), 6.94(1H, d, J=8.5 Hz), 7.35(1H, dd, J=8.5, 2.0 Hz), 7.48(1H, d, J=2.0 Hz), 8.20(1H, d, J=9.0 Hz), 8.55(1H, dd, J=9.0, 2.0 Hz), 8.65(1H, d, J=2.0 Hz)

Example 56

1-(4-Carboxypiperidino)-4-(3-chloro-4-methoxybenzyl)amino-6-nitrophthalazine hydrochloride

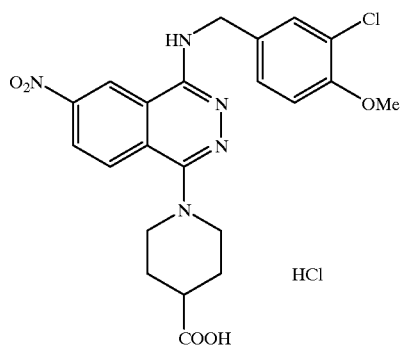

1-(4-Carboxypiperidino)-4-(3-chloro-4-methoxybenzyl) amino-6-nitrophthalazine was prepared from the compound prepared in Example 55 in a similar manner to that of Example 43 and further converted into the title compound in the same manner as that employed in Example 4 for the formation of hydrochloride.

M.p.: 137–143 (dec.) ° C.

MASS: 472 (MH+)

1H-NMR (400 MHz, DMSO-d6) δ: 1.85–1.92(2H, m), 1.97–2.05(2H, m), 2.50–2.60(1H, m), 2.96–3.03(2H, m), 3.52–3.56(2H, m), 3.86(3H, s), 4.75(2H, d, J=4.5 Hz), 7.18(1H, d, J=8.5 Hz), 7.46(1H, m), 7.61(1H, d, J=2.0 Hz), 8.36(1H, d, J=9.0 Hz), 8.76(1H, dd, J=9.0, 2.0 Hz), 9.70(1H, m)

Example 57

1-Chloro-4-(3,4-methylenedioxybenzyl)amino-6-nitrophthalazine

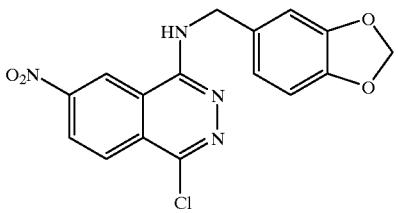

In a similar manner to that of Example 1, the title compound was prepared from 1,4-dichloro-6-nitrophthalazine prepared in Preparative Example 8.

M.p.: 186.5–188.0° C.

MASS: 359 (MH+)

1H-NMR (400 MHz, CDCl3) δ: 4.80(2H, d, J=5.0 Hz), 5.73(1H, t, J=5.0 Hz), 5.95(2H, s), 6.78(1H, d, J=8.0 Hz), 6.92(1H, dd, J=8.0, 2.0 Hz), 6.94(1H, d, J=2.0 Hz), 8.37(1H, d, J=9.0 Hz), 8.64(1H, dd, J=9.0, 2.0 Hz), 8.73(1H, d, J=2.0 Hz)

Example 58

4-Chloro-1-(3,4-methylenedioxybenzyl)amino-6-nitrophthalazine

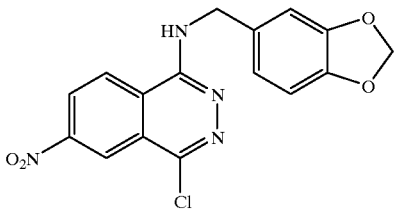

In a similar manner to that of Example 2, the title compound was prepared from 1,4-dichloro-6-nitrophthalazine prepared in Preparative Example 8.

M.p.: 240–242 (dec.) ° C.

MASS: 359 (MH+)

1H-NMR (400 MHz, CDCl3) δ: 4.78(2H, d, J=5.0 Hz), 5.52(1H, t, J=5.0 Hz), 5.96(2H, s), 6.78(1H, d, J=8.0 Hz), 6.91(1H, dd, J=8.0, 1.5 Hz), 6.93(1H, d, J=1.5 Hz), 7.98(1H, d, J=9.0 Hz), 8.59(1H, dd, J=9.0, 2.0 Hz), 9.05(1H, d, J=2.0 Hz)

Example 59

1-(4-Dimethylaminopiperidino)-4-(3,4-methylene-dioxybenzyl)amino-6-nitrophthalazine

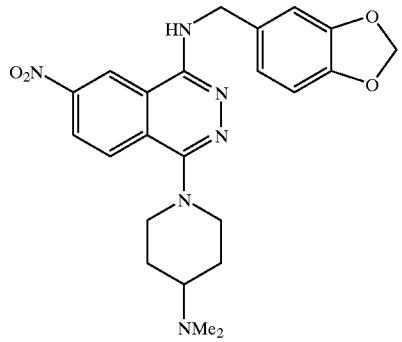

In a similar manner to that of Example 3, the title compound was prepared from 1-chloro-4-(3,4-methylenedioxybenzyl)amino-6-nitrophthalazine prepared in Example 57.

M.p.: 105.0–107.0° C.

MASS: 451 (MH+)

1H-NMR (400 MHz, CDCl3) δ: 1.79(2H, ddd, J=13.0, 13.0, 4.0 Hz), 2.04(2H, d, J=13.0 Hz), 2.31–2.40(1H, m), 2.38(6H, s), 3.03(2H, dt, J=13.5, 1.5 Hz), 3.66(2H, d, J=13.5 Hz), 4.77(2H, d, J=5.0 Hz), 5.15(1H, t, J=5.0 Hz), 5.98(2H, s), 6.82(1H, d, J=8.0 Hz), 6.94(1H, dd, J=8.0, 1.5 Hz), 6.97(1H, d, J=1.5 Hz), 8.19(1H, d, J=9.0 Hz), 8.54(1H, dd, J=9.0, 2.0 Hz), 8.63(1H, d, J=2.0 Hz)

Example 60

1-(Imidazol-1-yl)-4-(3,4-methylenedioxybenzyl)amino-6-nitrophthalazine

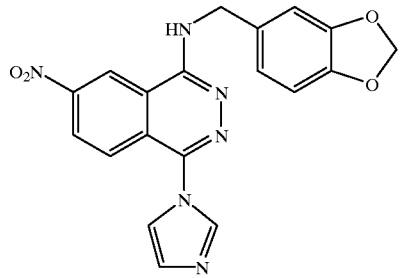

In a similar manner to that of Example 3, the title compound was prepared from 1-chloro-4-(3,4-methylenedioxybenzyl)amino-6-nitrophthalazine prepared in Example 57.

M.p.: 154.0–155.5° C.

MASS: 391 (MH+)

1H-NMR (400 MHz, CDCl3) δ: 4.89(2H, d, J=5.5 Hz), 5.97(2H, s), 6.05(1H, t, J=5.5 Hz), 6.82(1H, d, J=8.0 Hz), 6.96(1H, dd, J=8.0, 2.0 Hz), 6.98(1H, d, J=2.0 Hz), 7.35(1H, s), 7.44(1H, s), 7.99(1H, d, J=9.0 Hz), 8.02(1H, s), 8.61(1H, dd, J=9.0, 2.0 Hz), 8.85(1H, d, J=2.0 Hz)

Example 61

1-(4-Ethoxycarbonylpiperidino)-4-(3,4-methylene-dioxybenzyl)amino-6-nitrophthalazine

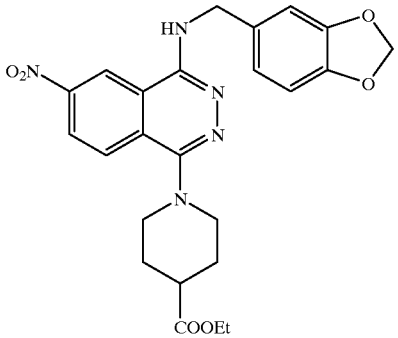

In a similar manner to that of Example 3, the title compound was prepared from the compound prepared in Example 57.

M.p.: 220–222° C.

MASS: 480 (MH+)

1H-NMR (400 MHz, CDCl3) δ: 1.30(3H, t, J=7.0 Hz), 1.99–2.16(4H, m), 2.52–2.60(1H, m), 3.03–3.11(2H, m), 3.57–3.63(2H, m), 4.20(2H. q, J=7.0 Hz), 4.77(2H, d, J=5.0 Hz), 5.17(1H, t, J=5.0 Hz), 5.98(2H, s), 6.82(1H, d, J=8.0 Hz), 6.94(1H, dd, J=8.0, 1.5 Hz), 6.97(1H, d, J=1.5 Hz), 8.20(1H, d, J=9.0 Hz), 8.54(1H, dd, J=9.0, 2.0 Hz), 8.64(1H, d, J=2.0 Hz)

Example 62

Potassium salt of 1-(4-carboxypiperidino)-4-(3,4-methylenedioxybenzyl)amino-6-nitrophthalazine

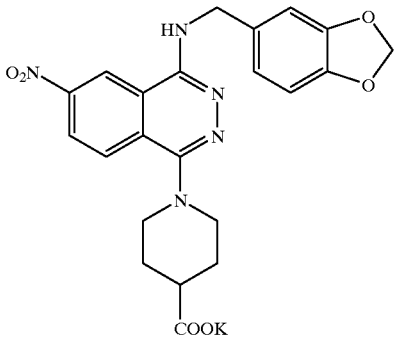

Potassium hydroxide (0.5 g) was dissolved in 30 ml of 50% aqueous methanol, followed by the addition of 0.26 g of the compound prepared in Example 61. The obtained mixture was stirred at room temperature for 4 hours.

The solvent was distilled away in a vacuum and water was added to the residue to form a solution. This solution was neutralized with dilute hydrochloric acid to precipitate a solid. This solid was recovered by filtration and dissolved in an aqueous solution of potassium carbonate. The obtained solution was adsorbed on an octadecylsilanol column and eluted with water/methanol to conduct purification. The obtained solid was crystallized from ethanol/ethyl acetate to give 0.15 g of the title compound as a pale-yellow solid.

M.p.: 206–209° C. (dec.)

1H-NMR (400 MHz, DMSO-d6) δ: 1.64–1.76(2H, m), 1.76–1.84(2H, m), 1.84–1.92(1H, m), 2.65–2.73(2H, m), 3.26–3.32(2H, m), 4.53(2H, d, J=5.5 Hz), 5.90(1H, t, J=5.5 Hz), 5.92(2H, s), 6.82(1H, d, J=8.0 Hz), 6.85(1H, dd, J=8.0, 1.0 Hz), 6.95(1H, d, J=1.0 Hz), 7.04(1H, d, J=2.0 Hz), 7.09(1H, dd, J=9.0, 2.0 Hz), 7.64(1H, d, J=9.0 Hz)

Example 63

6-Amino-1-(4-ethoxycarbonylpiperidino)-4-(3,4-methylenedioxybenzyl)aminophthalazine hydrochloride

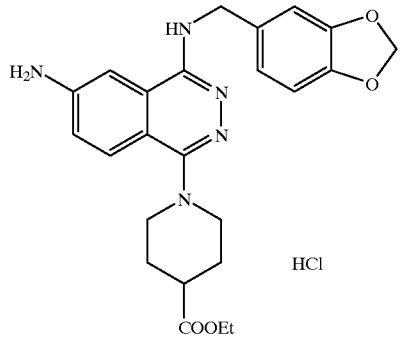

The compound (0.70 g) prepared in Example 61 was suspended in 50 ml of ethanol, followed by the addition of 50 ml of 10% palladium/carbon. The obtained mixture was stirred in a hydrogen atmosphere of 1 atm overnight and filtered to remove the catalyst. The filtrate was concentrated in a vacuum and the residue was dissolved in ethyl acetate. An excess of a 4N solution of hydrochloric acid in ethyl acetate was added to the obtained solution to form a hydrochloride. The solvent was distilled away in a vacuum. The obtained residue was recrystallized from ethanol/diisopropyl ether to give 0.54 g of the title compound as a white powder.

M.p.: 156.5–158.5° C.

MASS: 450 (MH+)

1H-NMR (400 MHz, CD3OD) δ: 1.28(3H, t, J=7.0 Hz), 1.95–2.03(2H, m), 2.04–2.12(2H, m), 2.57–2.65(1H, m), 2.99–3.11(2H, m), 3.60–3.68(2H, m), 4.17(2H, q, J=7.0 Hz), 4.62(2H, s), 5.94(2H, s), 6.80(1H, d, J=8.0 Hz), 6.89(1H, dd, J=8.0, 2.0 Hz), 6.92(1H, d, J=2.0 Hz), 7.29(1H, br s), 7.31(1H, d, J=9.0 Hz), 7.90(1H, d, J=9.0 Hz)

Example 64

1-(3-Chloro-4-methoxybenzyl)amino-4,6,7-trichlorophthalazine

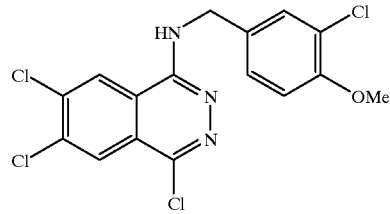

In a similar manner to that of Example 1, the title compound was prepared from 1,4,6,7-tetrachlorophthalazine.

M.p.: 208–209° C.

MASS: 404 (MH+)

1H-NMR (400 MHz, CDCl3) δ: 3.90(3H, s), 4.77(2H, d, J=5.0 Hz), 5.29(1H, t, J=5.0 Hz), 6.91(1H, d, J=8.0 Hz), 7.32(1H, dd, J=8.0, 2.0 Hz), 7.45(1H, d, J=2.0 Hz), 7.89(1H, s), 8.28(1H, s)

Example 65

1-(3-Chloro-4-methoxybenzyl)amino-6,7-dichloro-4-(4-hydroxypiperidino)phthalazine hydrochloride

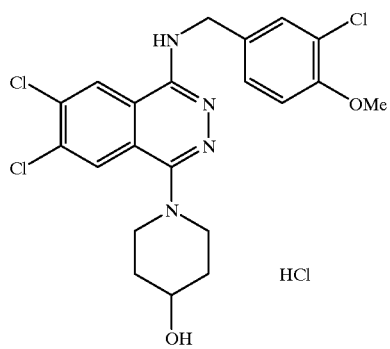

In a similar manner to that of Example 4, the title compound was prepared from the compound prepared in Example 64.

M.p.: 174.0–175.5° C.

MASS: 467 (MH+)

1H-NMR (400 MHz, DMSO-d6) δ: 1.63–1.73(2H, m), 1.91–1.99(2H, m), 3.00–3.08(2H, m), 3.39–3.49(2H, m), 3.73–3.81(1H, m), 3.86(3H, s), 4.71(2H, d, J=6.0 Hz), 7.14(1H, d, J=8.5 Hz), 7.45(1H, dd, J=8.5, 2.0 Hz), 7.59(1H, d, J=2.0 Hz), 8.16(1H, s), 9.26(1H, s)

Example 66

1-(3-Chloro-4-methoxybenzyl)amino-6,7-dichloro-4-(4-ethoxycarbonylpiperidino)phthalazine

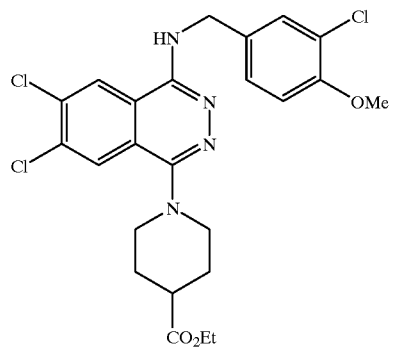

In a similar manner to that of Example 3, the title compound was prepared from the compound prepared in Example 64.

1H-NMR (400 MHz, CDCl3) δ: 1.29(3H, t, J=7.0 Hz), 1.96–2.13(4H, m), 2.48–2.55(1H, m), 3.98-3.05(2H, m), 3.53–3.58(2H, m), 3.86(3H, s), 4.19(2H, q, J=7.0 Hz), 4.71(2H, d, J=5.0 Hz), 5.31(1H, t, J=5.0 Hz), 6.84(1H, d, J=8.5 Hz), 7.27(1H, dd, J=8.5, 2.0 Hz), 7.40(1H, d, J=2.0 Hz), 7.94(1H, s), 8.08(1H, s)

Example 67

1-(4-Carboxypiperidino)-4-(3-chloro-4-methoxybenzyl)amino-6,7-dichlorophthalazine

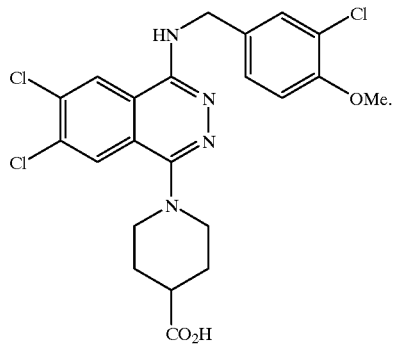

In a similar manner to that of Example 43, the title compound was prepared from the compound prepared in Example 66.

M.p.: 268–273 (dec.) ° C.

MASS: 495 (MH+)

1H-NMR (400 MHz, DMSO-d6) δ: 1.80–1.90(2H, m), 1.93–2.00(2H, m), 2.40–2.50(1H, m), 3.84–3.91(2H, m), 3.30–3.45(2H, m), 3.82(3H, s), 4.62(2H, d, J=5.5 Hz), 7.10(1H, d, J=8.5 Hz), 7.34(1H, dd, J=8.5, 2.0 Hz), 7.44(1H, d, J=2.0 Hz), 7.85(1H, t, J=5.5 Hz), 8.05(1H, s), 8.68(1H, s)

Example 68

6-Chloro-1-(3-chloro-4-methoxybenzyl)amino-4-(3-pyridylmethyl)phthalazine dihydrochloride

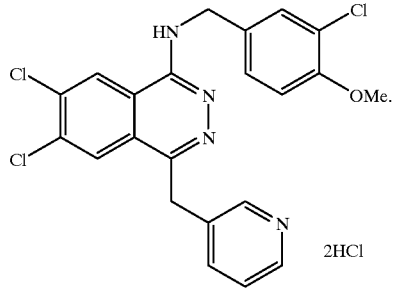

In a similar manner to that of Example 4, the title compound was prepared from the compound prepared in Preparative Example 11.

M.p.: 168.5–169.5° C.

MASS: 425 (MH+)

1H-NMR (400 MHz, DMSO-d6) δ: 3.83(3H, s), 4.77(2H, s), 4.79(2H, s), 7.13(1H, d, J=8.5 Hz), 7.47(1H, dd, J=8.5, 2.0 Hz), 7.62(1H, d, J=2.0 Hz), 7.89(1H, dd, J=7.5, 5.5 Hz), 8.26(1H, dd, J=9.0, 2.0 Hz), 8.34(1H, d, J=7.5 Hz), 8.51(1H, d, J=2.0 Hz), 8.76(1H, d, J=5.5 Hz), 8.87(1H, s), 9.12(1H, d, J=9.0 Hz), 11.01(1H, br s)

Example 69

6-Chloro-4-(3-chloro-4-methoxybenzyl)amino-1-(3-pyridylmethyl)phthalazine dihydrochloride

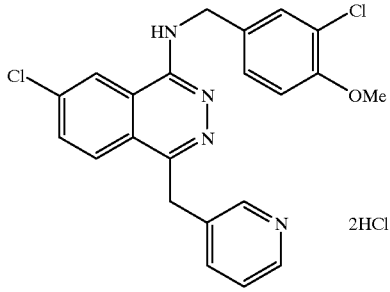

In a similar manner to that of Example 4, the title compound was prepared from the compound prepared in Preparative Example 12.

M.p.: 170.0–171.0° C.

MASS: 425 (MH+)

1H-NMR (400 MHz, DMSO-d6) δ: 3.85(3H, s), 4.78(2H, d, J=6.0 Hz), 4.81(2H, s), 7.13(1H, d, J=8.5 Hz), 7.48(1H, dd, J=8.5, 2.0 Hz), 7.62(1H, d, J=2.0 Hz), 7.95(1H, dd, J=8.0, 6.0 Hz), 8.25(1H, dd, J=8.5, 2.0 Hz), 8.40–8.46(2H, m), 8.81(1H, d, J=6.0 Hz), 8.93(1H, d, J=1.0 Hz), 9.26–9.31 (1H, m), 10.91(1H, br s)

Example 70

4-(4-Ethoxycarbonylpiperidino)-1-(3,4-methylenedioxybenzyl)aminopyrido[3,4-d]pyridazine

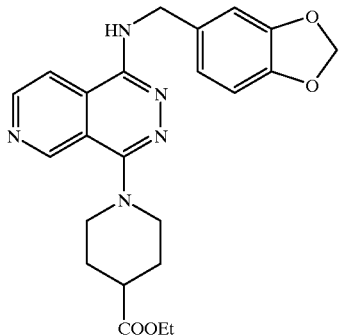

The title compound was prepared in a similar manner to that of Example 45.

M.p.: 135–136° C.

MASS: 436 (MH+)

1H-NMR (400 MHz, CDCl3) δ: 1.30(3H, t, J=7.0 Hz), 2.00–2.16(4H, m), 2.52–2.59(1H, m), 3.07–3.14(2H, m), 3.69–3.71(2H, m), 4.19(2H, q, J=7.0 Hz), 4.74(2H, d, J=5.0 Hz), 5.00(1H, t, J=5.0 Hz), 5.96(2H, s), 6.80(1H, d, J=8.0 Hz), 6.91(1,H, dd, J=8.0, 1.5 Hz), 6.94(1H, d, J=1.5 Hz), 7.48(1H, dd, J=5.5, 1.0 Hz), 8.93(1H, d, J=5.5 Hz), 9.42(1H, d, J=1.0 Hz)

Example 71

1-(4-Ethoxycarbonylpiperidino)-4-(3,4-methylenedioxybenzyl)aminopyrido[3,4-d]pyridazine

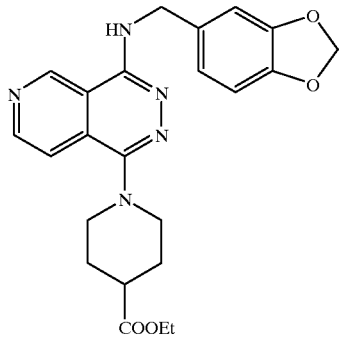

The title compound was prepared in a similar manner to that of Example 46.

M.p.: 119–120.5° C.

MASS: 436 (MH+)

1H-NMR (400 MHz, CDCl3) δ: 1.30(3H, t, J=7.0 Hz), 1.97–2.15(4H, m), 2.51–2.59(1H, m), 3.01–3.08(2H, m), 3.61–3.67(2H, m), 4.19(2H, q, J=7.0 Hz), 4.78(2H, d, J=5.0 Hz), 5.24(1H, t, J=5.0 Hz), 5.97(2H, s), 6.81(1H, d, J=8.0 Hz), 6.93(1H, dd, J=8.0, 1.5 Hz), 6.97(1H, d, J=1.5 Hz), 7.75(1H, dd, J=5.5, 1.0 Hz), 8.93(1H, d, J=5.5 Hz), 9.21(1H, d, J=1.0 Hz)

Example 72

4-(4-Carboxypiperidino)-1-(3,4-methylenedioxybenzyl)aminopyrido[3,4-d]pyridazine

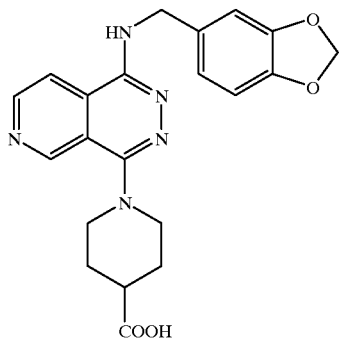

In a similar manner to that of Example 43, the title compound was prepared from the compound prepared in Example 70.

M.p.: 138–140° C.

MASS: 408 (MH+)

1H-NMR (400 MHz, DMSO-d6) δ: 1.82–1.93(2H, m), 1.94–2.20(2H, m), 2.45–2.52(1H, m), 2.89–2.98(2H, m), 3.46–3.55(2H, m), 4.62(2H, d, J=5.5 Hz), 5.96(2H, s), 6.85(1H, d, J=8.0 Hz), 6.87(1H, dd, J=8.0, 1.0 Hz), 6.97(1H, d, J=1.0 Hz), 7.88(1H, t, J=5.5 Hz), 8.17(1H, d, J=5.5 Hz), 8.96(1H, d, J=5.5 Hz), 9.29 (1H, s), 12.25(1H, br s)

Example 73

1-(4-Carboxypiperidino)-4-(3,4-methylenedioxybenzyl)aminopyrido[3,4-d]pyridazine

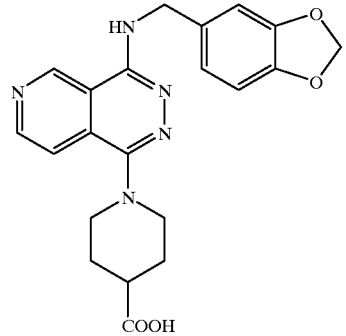

In a similar manner to that of Example 43, the title compound was prepared from the compound prepared in Example 71.

M.p.: 205–206° C.

MASS: 408 (MH+)

1H-NMR (400 MHz, DMSO-d6) δ: 1.80–1.91(2H, m), 1.94–2.01(2H, m), 2.42–2.50(1H, m), 2.84–2.92(2H, m), 3.42–3.48(2H, m), 4.64(2H, d, J=5.5 Hz), 5.97(2H, s), 6.85(1H, d, J=8.0 Hz), 6.89(1H, dd, J=8.0, 1.5 Hz), 6.99(1H, d, J=1.5 Hz), 7.76(1H, d, J=5.5 Hz), 8.05(1H, t, J=5.5 Hz), 8.93(1H, d, J=5.5 Hz), 9.67(1H, s)

What is claimed is:

1. A fused pyridazine compound represented by the general formula (II) or a pharmacologically acceptable salt thereof:

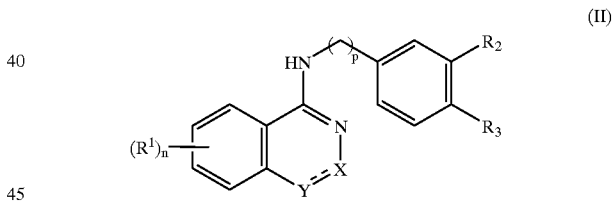

(II)

wherein n represents 1 or 2;

p represents 1, 2, or 3;

$R^1$ represents a halogen atom, a nitro group, an amino group, a cyano group or a 4-hydroxypiperidin-1-yl group;

$R^2$ and $R^3$ represent each independently a halogen atom, a lower alkyl group or a lower alkoxy group, or $R^2$ and $R^3$ may form a methylenedioxy ring together;

the bond illustrated by the following line:

--- represents a single bond or a double bond, and;

(1) when the above bond is a double bond;

then X represents a nitrogen atom, and Y represents a =C—Z group, wherein Z is selected from the group consisting of:

(i) a halogen atom, (ii) a group represented by the following formula:

$$-\left(N\underset{(CH_2)_{\overline{m}}-OH}{\overset{(CH_3)_p}{\diagup}}\right)$$

wherein p represents 0 or 1, and m represents 0, 1 or 2, (iii) a group represented by the following formula:

$$-\left(N\diagdown\diagup R^4\right)$$

wherein $R^4$ represents a carbamoyl group, a carboxy group, a carboxylate group with potassium atom, a lower alkoxycarbonyl group or a dialkylamino group, (iv) a group represented by the following formula:

$$-\left(\overset{R^5\quad R^6}{N\diagdown\diagup}\right)$$

wherein one of $R^5$ or $R^6$ represents a hydrogen atom and the other represents a hydroxy group, (v) a group represented by the following formula:

$$-\left(N\diagdown\diagup N-R^7\right)$$

wherein $R^7$ represents a pyridyl group, a pyrimidyl group or a lower hydroxyalkyl group, (vi) a group represented by the following formula:

$$\left(O=\diagdown\diagup N-\right)$$

wherein the bond illustrated by the following line:

- - - represents a either single bond or a double bond, (vii) a hydroxypyrrolidinyl group attached by way of the N atom;
(viii) a hydroxymethylpyrrolidinyl group attached by way of the N atom,
(ix) an imidazolyl group,
(x) a morpholinyl group attached by way of the N atom,
(xi) a pyridylmethyl group, (xii) a group represented by the following formula:

$$-\left(\overset{R^8}{N}-CH_2-R^9\right)$$

wherein $R^8$ represents a hydrogen atom or a lower alkyl group, $R^9$ represents a pyridyl group, a lower hydroxyalkyl group or a carboxyalkyl group,
(xiii) a lower alkoxy group, and
(xiv) a lower, hydroxyalkoxy group;

(2) when the above bond is a single bond;
then X represent a >$NR^{10}$ group,
wherein $R^{10}$ represents a hydrogen atom, carboxymethyl group, a lower alkoxycarbonylmethyl group, a tetrahydropyranylalkyl group or a hydroxyalkyl group,
and Y represents a carbonyl group,
with the proviso that compounds wherein n is 1, $R^1$ is a cyano group, $R^2$ and $R^3$ represent each independently a halogen atom or methoxy group, the bond illustrated by the line - - - is a double bond, X is a nitrogen atom and Y is a =C—Z group, where Z is a halogen atom or a group represented by the formula $$-N\diagdown\diagup-OH,$$

are excluded.

2. The compound according to claim 1, wherein Z is a hydroxypyrrolidinyl group or a hydroxymethylpyrrolidinyl group.

3. A fused pyridazine compound selected from the group consisting of 1-chloro-4-(3-chloro-4-methoxybenzyl) amino-6-cyanophthalazine, 4-chloro-1-(3-chloro-4-methoxybenzyl)amino-6-cyanophthalazine, 4-(3-chloro-4-methoxybenzyl)amino-6-cyano-1-(4-oxo-1,4-dihydropyrid-1-yl)phthalazine, 4-(3-chloro-4-methoxybenzyl)amino-6-cyano-1-[4-(hydroxymethyl)piperidino]phthalazine hydrochloride, 4-(3-chloro-4-methoxybenzyl)amino-6-cyano-1-(3-hydroxypropyl)aminophthalazine, 4-(3-chloro-4-methoxybenzyl)amino-6-cyano-1-[4-(2-hydroxyethyl) piperidino]phthalazine hydrochloride, 4-(3-chloro-4-methoxybenzyl)amino-6-cyano-1-(4-hydroxy-4-methylpiperidino)phthalazine hydrochloride, 4-(3-chloro-4-methoxybenzyl)amino-6-cyano-1-(3-hydroxypiperidino) phthalazine hydrochloride, 4-(3-chloro-4-methoxybenzyl) amino-6-cyano-1-(2-pyridylmethyl)aminophthalazine dihydrochloride, 4-(3-chloro-4-methoxybenzyl)amino-6-cyano-1-(4-pyridylmethyl)aminophthalazine dihydrochloride, 4-(3-chloro-4-methoxybenzyl)amino-6-cyano-1-(3-pyridylmethyl)aminophthalazine dihydrochloride, 4-(3-chloro-4-methoxybenzyl)amino-6-cyano-1-[N-(3-hydroxypropyl)-N-methylamino] phthalazine, 4-(3-chloro-4-methoxybenzyl)amino-6-cyano-1-[4-(2-pyridyl)piperazin-1-yl]phthalazine dihydrochloride, 4-(3-chloro-4-methoxybenzyl)amino-6-cyano-1-[4-(2-pyrimidyl)piperazin-1-yl]phthalazine dihydrochloride, 1-(4-carbamoylpiperidino)-4-(3-chloro-4-methoxybenzyl) amino-6-cyanophthalazine, 4-(3-chloro-4-methoxybenzyl) amino-6-cyano-1-[4-(2-hydroxyethyl)piperazin-1-yl] phthalazine dihydrochloride, 4-(3-chloro-4-methoxybenzyl) amino-6-cyano-1-(4-oxopiperidino)phthalazine hydrochloride, 1-(4-carboxypiperidino)-4-(3-chloro-4- methoxybenzyl)-amino-6-cyanophthalazine hydrochloride, 4-(3-chloro-4-methoxybenzyl)amino-6-cyano-1(2H)-phthalazinone, 2-tert-butoxycarbonylmethyl-4-(3-chloro-4-methoxybenzyl)amino-6-cyano-1(2H)-phthalazinone, 2-carboxymethyl-4-(3-chloro-4-methoxybenzyl)amino-6-cyano-1(2H)-phthalazinone, 4-(3-chloro-4-methoxybenzyl)amino-6-cyano-2-[3-(tetrahydropyran-2-yloxy)propyl]-1(2H)-phthalazinone 4-(3-chloro-4-methoxybenzyl)amino-6-cyano-2-(3-hydroxypropyl)-1(2H)-phthalazinone, 6-cyano-1-(4-hydroxypiperidino)-4-(3,4-methylenedioxybenzyl)aminophthalazine hydrochloride, 4-(3-chloro-4-methoxybenzylamino-1,6-dichlorophthalazine, 1-(3-chloro-4-methoxybenzyl)amino-4,6-dichlorophthalazine, 6-chloro-4-(3-chloro-4-methoxybenzyl)amino-1-(3-hydroxypyrrolidino)phthalazine, (R)-6-chloro-4-(3-chloro-4-methoxybenzyl)amino-1-[2-(hydroxymethyl)pyrrolidino]phthalazine hydrochloride, 6-chloro-4-(3-chloro-4-methoxybenzyl)amino-1-(imidazol-1-yl)phthalazine, 6-chloro-4-(3-chloro-4-methoxybenzyl)amino-1-(4-hydroxypiperidino)phthalazine hydrochloride, 1,6-bis-(4-hydroxypiperidino)-4-(3-chloro-4-methoxybenzyl)aminophthalazine, 6-chloro-4-(3-chloro-4-methoxybenzyl)amino-1-morpholinophthalazine hydrochloride, 6-chloro-4-(3-chloro-4-methoxybenzyl)amino-1-( 3-hydroxypropyl)aminophthalazine, 6-chloro-4-(3-chloro-4-methoxybenzyl)amino-1-[4-(hydroxymethyl)piperidino]phthalazine, 6-chloro-4-(3-chloro-4-methoxybenzyl)amino-1-[4-(2-hydroxyethyl)piperidino]phthalazine, 6-chloro-4-(3-chloro-4-methoxybenzyl)amino-1-ethoxyphthalazine, 6-chloro-4-(3-chloro-4-methoxybenzyl)amino-1-(3-hydroxypropyloxy)phthalazine, 6-chloro-4-(3-chloro-4-methoxybenzyl)amino-1-[N-(3-hydroxypropyl)-N-methylamino]phthalazine, 6-chloro-4-(3-chloro-4-methoxybenzyl)amino-1-(4-oxopiperidino)phthalazine hydrochloride, 6-chloro-4-(3-chloro-4-methoxybenzyl)amino-1-(4-ethoxycarbonylpiperidino)phthalazine, 1-(4-carboxypiperidino)-6-chloro-4-(3-chloro-4-methoxybenzyl)aminophthalazine, 1-[N-(3-carboxypropyl)-N-methylamino]-6-chloro-4-(3-chloro-4-methoxybenzyl)aminophthalazine, 6-chloro-1-(4-ethoxycarbonylpiperidino)-4-(3,4-methylenedioxybenzyl)aminophthalazine, 6-chloro-4-(4-ethoxycarbonylpiperidino)-1-(3,4-methylenedioxybenzyl)aminophthalazine, 1-(4-carboxypiperidino)-6-chloro-4-(3,4-methylenedioxybenzyl)aminophthalazine, 4-(4-carboxypiperidino)-6-chloro-1-(3,4-methylenedioxybenzyl)aminophthalazine, 1-chloro-4-(3-chloro-4-methoxybenzyl)amino-6-nitrophthalazine, 4-chloro-1-(3-chloro-4-methoxybenzyl)amino-6-nitrophthaline, 4-(3-chloro-4-methoxybenzyl)amino-1-(4-hydroxypiperidino)-6-nitrophthalazine hydrochloride, 4-(3-chloro-4-methoxybenzyl)amino-1-[4-(hydroxymethyl)piperidino]-6-nitrophthalazine hydrochloride, 4-(3-chloro-4-methoxybenzyl)amino-1-[4-(2-hydroxyethyl)piperidino]-6-nitrophthalazine hydrochloride, 4-(3-chloro-4-methoxybenzyl)amino-1-[4-(2-hydroxyethyl)piperazin-1-yl]-6-nitrophthalazine, 1-(4-ethoxycarbonylpiperidino)-4-(3-chloro-4-methoxybenzyl)amino-6-nitrophthalazine, 1-(4-carboxypiperidino)-4-(3-chloro-4-methoxybenzyl)amino-6-nitrophthalazine hydrochloride, 1-chloro-4-(3,4-methylenedioxybenzyl)amino-6-nitrophthalazine, 4-chloro-1-(3,4-methylenedioxybenzyl)amino-6-nitrophthalazine, 1-(4-dimethylaminopiperidino)-4-(3,4-methylenedioxybenzyl)amino-6-nitrophthalazine, 1-(imidazol-1-yl)-4-(3,4-methylenedioxybenzyl)amino-6-nitrophthalazine, 1-(4-ethoxycarbonylpiperidino)-4-(3,4-methylenedioxybenzyl)amino-6-nitrophthalazine, potassium salt of 1-(4-carboxypiperidino)-4-(3,4-methylenedioxybenzyl)amino-6-nitrophthalazine, 6-amino-1-(4-ethoxycarbonylpiperidino)-4-(3,4-methylenedioxybenzyl)aminophthalazine hydrochloride, 1-(3-chloro-4-methoxybenzyl)amino-4,6,7-trichlorophthalazine, 1-(3-chloro-4-methoxybenzyl)amino-6,7-dichloro-4-(4-hydroxypiperidino)phthalazine hydrochloride, 1-(3-chloro-4-methoxybenzyl)amino-6,7-dichloro-4-(4-ethoxycarbonylpiperidino)phthalazine, 1-(4-carboxypiperidino)-4-(3-chloro-4-methoxybenzyl)amino-6,7-dichlorophthalazine, 6-chloro-1-(3-chloro-4-methoxybenzyl)amino-4-(3-pyridylmethyl)phthalazine dihydrochloride, and 6-chloro-4-(3-chloro-4-methoxybenzyl)amino-1-(3-pyridylmethyl)phthalazine dihydrochloride.

4. A pharmaceutical composition, comprising the compound according to claim 1, and a pharmaceutically acceptable carrier therefor.

5. A method for treating diseases for which an antiplatelet action is efficacious comprising administering an effective amount of the compound according to claim 1 to a patient in need thereof.

6. A method for treating hypertension comprising administering an effective amount of the compound according to claim 1 to a patient in need thereof.

\* \* \* \* \*